(12) United States Patent
Weiss

(10) Patent No.: US 7,998,438 B2
(45) Date of Patent: Aug. 16, 2011

(54) ZONE REACTOR INCORPORATING REVERSIBLE HYDROGEN HALIDE CAPTURE AND RELEASE

(75) Inventor: Michael Joseph Weiss, Skokie, IL (US)

(73) Assignee: GRT, Inc., Santa Barbara, CA (US)

( * ) Notice: Subject to any disclaimer, the term of this patent is extended or adjusted under 35 U.S.C. 154(b) by 538 days.

(21) Appl. No.: 12/127,702

(22) Filed: May 27, 2008

(65) Prior Publication Data

US 2009/0127163 A1    May 21, 2009

Related U.S. Application Data

(60) Provisional application No. 60/931,891, filed on May 24, 2007.

(51) Int. Cl.
*B01J 8/04* (2006.01)

(52) U.S. Cl. ......... 422/630; 422/634; 422/638; 422/644

(58) Field of Classification Search ............. 422/191, 422/630, 634, 638, 644; 585/310, 323, 408; 568/891
See application file for complete search history.

(56) References Cited

U.S. PATENT DOCUMENTS

| | | | |
|---|---|---|---|
| 2,168,260 A | 8/1939 | Heisel et al. |
| 2,246,082 A | 6/1941 | Vaughan et al. |
| 2,488,083 A | 11/1949 | Gorin et al. |
| 2,677,598 A | 5/1954 | Crummett et al. |
| 2,941,014 A | 6/1960 | Rothweiler et al. |
| 3,076,784 A | 2/1963 | Huermann et al. |
| 3,172,915 A | 3/1965 | Borkowski et al. |
| 3,246,043 A | 4/1966 | Rosset et al. |
| 3,273,964 A | 9/1966 | Rosset |
| 3,294,846 A | 12/1966 | Livak et al. |
| 3,310,380 A | 3/1967 | Lester |
| 3,346,340 A | 10/1967 | Louver et al. |
| 3,353,916 A | 11/1967 | Lester |
| 3,353,919 A | 11/1967 | Stockman |
| 3,496,242 A | 2/1970 | Berkowitz et al. |
| 3,562,321 A | 2/1971 | Borkowski et al. |
| 3,598,876 A | 8/1971 | Bloch |
| 3,657,367 A | 4/1972 | Blake et al. |
| 3,670,037 A | 6/1972 | Dugan |

(Continued)

FOREIGN PATENT DOCUMENTS

BR    0210054    8/2004

(Continued)

OTHER PUBLICATIONS

U.S. Appl. No. 60/487,364, filed Jul. 15, 2003, Lorkovic et al.

(Continued)

*Primary Examiner* — N. Bhat

(74) *Attorney, Agent, or Firm* — Baker Botts L.L.P.

(57) ABSTRACT

An improved process and a zone reactor for converting a hydrocarbon feedstock into higher hydrocarbons is provided. A first zone in the reactor contains both a material capable of releasing hydrogen halide (HX) and a carbon-carbon coupling catalyst; a second zone is initially empty or contains a halogenation and/or oxyhalogenation catalyst; and a third zone contains both a carbon-carbon coupling catalyst and a material capable of capturing HX. Air or oxygen is introduced into the first zone, a feedstock is introduced into the second zone, and products are produced in the third zone. HX produced during the reaction is reversibly captured and released in zones 1 and 3.

32 Claims, 1 Drawing Sheet

U.S. PATENT DOCUMENTS

| | | | |
|---|---|---|---|
| 3,673,264 A | 6/1972 | Kuhn | |
| 3,679,758 A | 7/1972 | Schneider | |
| 3,702,886 A | 11/1972 | Argauer et al. | |
| 3,705,196 A | 12/1972 | Turner | |
| 3,799,997 A | 3/1974 | Schmerling | |
| 3,865,886 A | 2/1975 | Schindler et al. | |
| 3,876,715 A | 4/1975 | McNulty et al. | |
| 3,879,473 A | 4/1975 | Stapp | |
| 3,879,480 A | 4/1975 | Riegel et al. | |
| 3,883,651 A | 5/1975 | Woitun et al. | |
| 3,886,287 A | 5/1975 | Kobayashi et al. | |
| 3,894,103 A | 7/1975 | Chang et al. | |
| 3,894,104 A | 7/1975 | Chang et al. | |
| 3,894,105 A | 7/1975 | Chang et al. | |
| 3,894,107 A | 7/1975 | Butter et al. | |
| 3,907,917 A | 9/1975 | Forth | |
| 3,919,336 A | 11/1975 | Kurtz | |
| 3,920,764 A | 11/1975 | Riegel et al. | |
| 3,923,913 A | 12/1975 | Antonini et al. | |
| 3,928,483 A | 12/1975 | Chang et al. | |
| 3,965,205 A | 6/1976 | Garwood et al. | |
| 3,974,062 A | 8/1976 | Owen et al. | |
| 3,987,119 A | 10/1976 | Kurtz et al. | |
| 3,992,466 A | 11/1976 | Plank et al. | |
| 4,006,169 A | 2/1977 | Anderson et al. | |
| 4,011,278 A | 3/1977 | Plank et al. | |
| 4,025,571 A | 5/1977 | Lago | |
| 4,025,572 A | 5/1977 | Lago | |
| 4,025,575 A | 5/1977 | Chang et al. | |
| 4,025,576 A | 5/1977 | Chang et al. | |
| 4,035,285 A | 7/1977 | Owen et al. | |
| 4,035,430 A | 7/1977 | Dwyer et al. | |
| 4,039,600 A | 8/1977 | Chang | |
| 4,044,061 A | 8/1977 | Chang et al. | |
| 4,046,825 A | 9/1977 | Owen et al. | |
| 4,049,734 A | 9/1977 | Garwood et al. | |
| 4,052,471 A | 10/1977 | Pearsall | |
| 4,052,472 A | 10/1977 | Givens et al. | |
| 4,058,576 A | 11/1977 | Chang et al. | |
| 4,060,568 A | 11/1977 | Rodewald | |
| 4,071,753 A | 1/1978 | Fulenwider et al. | |
| 4,072,733 A | 2/1978 | Hargis et al. | |
| 4,087,475 A | 5/1978 | Jordan | |
| 4,088,706 A | 5/1978 | Kaeding | |
| 4,092,368 A | 5/1978 | Smith | |
| 4,110,180 A | 8/1978 | Nidola et al. | |
| 4,117,251 A | 9/1978 | Kaufhold et al. | |
| 4,129,604 A | 12/1978 | Tsao | |
| 4,133,838 A | 1/1979 | Pearson | |
| 4,133,966 A | 1/1979 | Pretzer et al. | |
| 4,138,440 A | 2/1979 | Chang et al. | |
| 4,156,698 A | 5/1979 | Dwyer et al. | |
| 4,169,862 A | 10/1979 | Eden | |
| 4,172,099 A | 10/1979 | Severino | |
| 4,187,255 A | 2/1980 | Dodd | |
| 4,194,990 A | 3/1980 | Pieters et al. | |
| 4,197,420 A | 4/1980 | Ferraris et al. | |
| 4,219,680 A | 8/1980 | Konig et al. | |
| 4,249,031 A | 2/1981 | Drent et al. | |
| 4,270,929 A | 6/1981 | Dang Vu et al. | |
| 4,272,338 A | 6/1981 | Lynch et al. | |
| 4,282,159 A | 8/1981 | Davidson et al. | |
| 4,300,005 A | 11/1981 | Li | |
| 4,300,009 A | 11/1981 | Haag et al. | |
| 4,301,253 A | 11/1981 | Warren | |
| 4,302,619 A | 11/1981 | Gross et al. | |
| 4,307,261 A | 12/1981 | Beard, Jr. et al. | |
| 4,308,403 A | 12/1981 | Knifton | |
| 4,311,865 A | 1/1982 | Chen et al. | |
| 4,317,800 A | 3/1982 | Sloterdijk et al. | |
| 4,317,934 A | 3/1982 | Seemuth | |
| 4,317,943 A | 3/1982 | Knifton | |
| 4,320,241 A | 3/1982 | Frankiewicz | |
| 4,333,852 A | 6/1982 | Warren | |
| 4,347,391 A | 8/1982 | Campbell | |
| 4,350,511 A | 9/1982 | Holmes et al. | |
| 4,371,716 A | 2/1983 | Paxson et al. | |
| 4,373,109 A | 2/1983 | Olah | |
| 4,376,019 A | 3/1983 | Gamlen et al. | |
| 4,380,682 A | 4/1983 | Leitert et al. | |
| 4,384,159 A | 5/1983 | Diesen | |
| 4,389,391 A | 6/1983 | Dunn, Jr. | |
| 4,410,714 A | 10/1983 | Apanel | |
| 4,412,086 A | 10/1983 | Beard, Jr. et al. | |
| 4,418,236 A | 11/1983 | Cornelius et al. | |
| 4,431,856 A | 2/1984 | Daviduk et al. | |
| 4,433,189 A | 2/1984 | Young | |
| 4,433,192 A | 2/1984 | Olah | |
| 4,439,409 A | 3/1984 | Puppe et al. | |
| 4,440,871 A | 4/1984 | Lok et al. | |
| 4,443,620 A | 4/1984 | Gelbein et al. | |
| 4,462,814 A | 7/1984 | Holmes et al. | |
| 4,465,884 A | 8/1984 | Degnan et al. | |
| 4,465,893 A | 8/1984 | Olah | |
| 4,467,130 A | 8/1984 | Olah | |
| 4,467,133 A | 8/1984 | Chang et al. | |
| 4,489,210 A | 12/1984 | Judat et al. | |
| 4,489,211 A | 12/1984 | Ogura et al. | |
| 4,492,657 A | 1/1985 | Heiss | |
| 4,496,752 A | 1/1985 | Gelbein et al. | |
| 4,497,967 A | 2/1985 | Wan | |
| 4,499,314 A | 2/1985 | Seddon et al. | |
| 4,506,105 A | 3/1985 | Kaufhold | |
| 4,509,955 A | 4/1985 | Hayashi | |
| 4,513,092 A | 4/1985 | Chu et al. | |
| 4,513,164 A | 4/1985 | Olah | |
| 4,523,040 A | 6/1985 | Olah | |
| 4,524,227 A | 6/1985 | Fowles et al. | |
| 4,524,228 A | 6/1985 | Fowles et al. | |
| 4,524,231 A | 6/1985 | Fowles et al. | |
| 4,538,014 A | 8/1985 | Miale et al. | |
| 4,538,015 A | 8/1985 | Miale et al. | |
| 4,540,826 A | 9/1985 | Banasiak et al. | |
| 4,543,434 A | 9/1985 | Chang | |
| 4,544,781 A | 10/1985 | Chao et al. | |
| 4,547,612 A | 10/1985 | Tabak | |
| 4,550,217 A | 10/1985 | Graziani et al. | |
| 4,550,218 A | 10/1985 | Chu | |
| 4,568,660 A | 2/1986 | Klosiewicz | |
| 4,579,977 A | 4/1986 | Drake | |
| 4,579,992 A | 4/1986 | Kaufhold et al. | |
| 4,579,996 A | 4/1986 | Font Freide et al. | |
| 4,587,375 A | 5/1986 | Debras et al. | |
| 4,588,835 A | 5/1986 | Torii et al. | |
| 4,590,310 A | 5/1986 | Townsend et al. | |
| 4,599,474 A | 7/1986 | Devries et al. | |
| 4,605,796 A | 8/1986 | Isogai et al. | |
| 4,605,803 A | 8/1986 | Chang et al. | |
| 4,621,161 A | 11/1986 | Shihabi | |
| 4,621,164 A | 11/1986 | Chang et al. | |
| 4,633,027 A | 12/1986 | Owen et al. | |
| 4,634,800 A | 1/1987 | Withers, Jr. et al. | |
| 4,642,403 A | 2/1987 | Hyde et al. | |
| 4,642,404 A | 2/1987 | Shihabi | |
| 4,652,688 A | 3/1987 | Brophy et al. | |
| 4,654,449 A | 3/1987 | Chang et al. | |
| 4,655,893 A | 4/1987 | Beale | |
| 4,658,073 A | 4/1987 | Tabak | |
| 4,658,077 A | 4/1987 | Kolts et al. | |
| 4,665,259 A | 5/1987 | Brazdil et al. | |
| 4,665,267 A | 5/1987 | Barri | |
| 4,665,270 A | 5/1987 | Brophy et al. | |
| 4,675,410 A | 6/1987 | Feitler et al. | |
| 4,690,903 A | 9/1987 | Chen et al. | |
| 4,695,663 A | 9/1987 | Hall et al. | |
| 4,696,985 A | 9/1987 | Martin | |
| 4,704,488 A | 11/1987 | Devries et al. | |
| 4,704,493 A | 11/1987 | Devries et al. | |
| 4,709,108 A | 11/1987 | Devries et al. | |
| 4,720,600 A | 1/1988 | Beech, Jr. et al. | |
| 4,720,602 A | 1/1988 | Chu | |
| 4,724,275 A | 2/1988 | Hinnenkamp et al. | |
| 4,735,747 A | 4/1988 | Ollivier et al. | |
| 4,737,594 A | 4/1988 | Olah | |
| 4,748,013 A | 5/1988 | Saito et al. | |
| 4,769,504 A | 9/1988 | Noceti et al. | |
| 4,774,216 A | 9/1988 | Kolts et al. | |

| | | | | | |
|---|---|---|---|---|---|
| 4,775,462 A | 10/1988 | Imai et al. | 5,107,032 A | 4/1992 | Erb et al. |
| 4,777,321 A | 10/1988 | Harandi et al. | 5,107,051 A | 4/1992 | Pannell |
| 4,781,733 A | 11/1988 | Babcock et al. | 5,107,061 A | 4/1992 | Ou et al. |
| 4,783,566 A | 11/1988 | Kocal et al. | 5,108,579 A | 4/1992 | Casci |
| 4,788,369 A | 11/1988 | Marsh et al. | 5,118,899 A | 6/1992 | Kimble et al. |
| 4,788,377 A | 11/1988 | Chang et al. | 5,120,332 A | 6/1992 | Wells |
| 4,792,642 A | 12/1988 | Rule et al. | 5,132,343 A | 7/1992 | Zwecker et al. |
| 4,795,732 A | 1/1989 | Barri | 5,138,112 A | 8/1992 | Gosling et al. |
| 4,795,737 A | 1/1989 | Rule et al. | 5,139,991 A | 8/1992 | Taylor et al. |
| 4,795,843 A | 1/1989 | Imai et al. | 5,146,027 A | 9/1992 | Gaffney |
| 4,795,848 A | 1/1989 | Teller et al. | 5,157,189 A | 10/1992 | Karra |
| 4,804,797 A | 2/1989 | Minet et al. | 5,160,502 A | 11/1992 | Kimble et al. |
| 4,804,800 A | 2/1989 | Bortinger et al. | 5,166,452 A | 11/1992 | Gradl et al. |
| 4,808,763 A | 2/1989 | Shum | 5,175,382 A | 12/1992 | Hebgen et al. |
| 4,814,527 A | 3/1989 | Diesen | 5,178,748 A | 1/1993 | Casci et al. |
| 4,814,532 A | 3/1989 | Yoshida et al. | 5,185,479 A | 2/1993 | Stauffer |
| 4,814,535 A | 3/1989 | Yurchak | 5,188,725 A | 2/1993 | Harandi |
| 4,814,536 A | 3/1989 | Yurchak | 5,191,142 A | 3/1993 | Marshall et al. |
| 4,849,562 A | 7/1989 | Buhs et al. | 5,194,244 A | 3/1993 | Brownscombe et al. |
| 4,849,573 A | 7/1989 | Kaeding | 5,202,506 A | 4/1993 | Kirchner et al. |
| 4,851,602 A | 7/1989 | Harandi et al. | 5,202,511 A | 4/1993 | Salinas, III et al. |
| 4,851,606 A | 7/1989 | Ragonese et al. | 5,210,357 A | 5/1993 | Kolts et al. |
| 4,886,925 A | 12/1989 | Harandi | 5,215,648 A | 6/1993 | Zones et al. |
| 4,886,932 A | 12/1989 | Leyshon | 5,223,471 A | 6/1993 | Washecheck |
| 4,891,463 A | 1/1990 | Chu | 5,228,888 A | 7/1993 | Gmelin et al. |
| 4,895,995 A | 1/1990 | James, Jr. et al. | 5,233,113 A | 8/1993 | Periana et al. |
| 4,899,000 A | 2/1990 | Stauffer | 5,237,115 A | 8/1993 | Makovec et al. |
| 4,899,001 A | 2/1990 | Kalnes et al. | 5,243,098 A | 9/1993 | Miller et al. |
| 4,899,002 A | 2/1990 | Harandi et al. | 5,243,114 A | 9/1993 | Johnson et al. |
| 4,902,842 A | 2/1990 | Kalnes et al. | 5,245,109 A | 9/1993 | Kaminsky et al. |
| 4,925,995 A | 5/1990 | Robschlager | 5,254,772 A | 10/1993 | Dukat et al. |
| 4,929,781 A | 5/1990 | James, Jr. et al. | 5,254,790 A | 10/1993 | Thomas et al. |
| 4,939,310 A | 7/1990 | Wade | 5,264,635 A | 11/1993 | Le et al. |
| 4,939,311 A | 7/1990 | Washecheck et al. | 5,268,518 A | 12/1993 | West et al. |
| 4,945,175 A | 7/1990 | Hobbs et al. | 5,276,226 A | 1/1994 | Horvath et al. |
| 4,950,811 A | 8/1990 | Doussain et al. | 5,276,240 A | 1/1994 | Timmons et al. |
| 4,950,822 A | 8/1990 | Dileo et al. | 5,276,242 A | 1/1994 | Wu |
| 4,956,521 A | 9/1990 | Volles | 5,284,990 A | 2/1994 | Peterson et al. |
| 4,962,252 A | 10/1990 | Wade | 5,300,126 A | 4/1994 | Brown et al. |
| 4,973,776 A | 11/1990 | Allenger et al. | 5,306,855 A | 4/1994 | Periana et al. |
| 4,973,786 A | 11/1990 | Karra | 5,316,995 A | 5/1994 | Kaminsky et al. |
| 4,982,024 A | 1/1991 | Lin et al. | 5,319,132 A | 6/1994 | Ozawa et al. |
| 4,982,041 A | 1/1991 | Campbell | 5,334,777 A | 8/1994 | Miller et al. |
| 4,988,660 A | 1/1991 | Campbell | 5,345,021 A | 9/1994 | Casci et al. |
| 4,990,696 A | 2/1991 | Stauffer | 5,354,916 A | 10/1994 | Horvath et al. |
| 4,990,711 A | 2/1991 | Chen et al. | 5,354,931 A | 10/1994 | Jan et al. |
| 5,001,293 A | 3/1991 | Nubel et al. | 5,366,949 A | 11/1994 | Schubert |
| 5,004,847 A | 4/1991 | Beaver et al. | 5,371,313 A | 12/1994 | Ostrowicki |
| 5,013,424 A | 5/1991 | James, Jr. et al. | 5,382,704 A | 1/1995 | Krespan et al. |
| 5,013,793 A | 5/1991 | Wang et al. | 5,382,743 A | 1/1995 | Beech, Jr. et al. |
| 5,019,652 A | 5/1991 | Taylor et al. | 5,382,744 A | 1/1995 | Abbott et al. |
| 5,026,934 A | 6/1991 | Bains et al. | 5,385,718 A | 1/1995 | Casci et al. |
| 5,026,937 A | 6/1991 | Bricker | 5,395,981 A | 3/1995 | Marker |
| 5,026,944 A | 6/1991 | Allenger et al. | 5,399,258 A | 3/1995 | Fletcher et al. |
| 5,034,566 A | 7/1991 | Ishino et al. | 5,401,890 A | 3/1995 | Parks |
| 5,043,502 A | 8/1991 | Martindale et al. | 5,401,894 A | 3/1995 | Brasier et al. |
| 5,051,477 A | 9/1991 | Yu et al. | 5,406,017 A | 4/1995 | Withers, Jr. |
| 5,055,235 A | 10/1991 | Brackenridge et al. | 5,414,173 A | 5/1995 | Garces et al. |
| 5,055,633 A | 10/1991 | Volles | 5,430,210 A | 7/1995 | Grasselli et al. |
| 5,055,634 A | 10/1991 | Volles | 5,430,214 A | 7/1995 | Smith et al. |
| 5,059,744 A | 10/1991 | Harandi et al. | 5,430,219 A | 7/1995 | Sanfilippo et al. |
| 5,068,478 A | 11/1991 | Miller et al. | 5,436,378 A | 7/1995 | Masini et al. |
| 5,071,449 A | 12/1991 | Sircar | 5,444,168 A | 8/1995 | Brown |
| 5,071,815 A | 12/1991 | Wallace et al. | 5,446,234 A | 8/1995 | Casci et al. |
| 5,073,656 A | 12/1991 | Chafin et al. | 5,453,557 A | 9/1995 | Harley et al. |
| 5,073,657 A | 12/1991 | Warren | 5,456,822 A | 10/1995 | Marcilly et al. |
| 5,082,473 A | 1/1992 | Keefer | 5,457,255 A | 10/1995 | Kumata et al. |
| 5,082,816 A | 1/1992 | Teller et al. | 5,464,799 A | 11/1995 | Casci et al. |
| 5,085,674 A | 2/1992 | Leavitt | 5,465,699 A | 11/1995 | Voigt |
| 5,087,779 A | 2/1992 | Nubel et al. | 5,470,377 A | 11/1995 | Whitlock |
| 5,087,786 A | 2/1992 | Nubel et al. | 5,480,629 A | 1/1996 | Thompson et al. |
| 5,087,787 A | 2/1992 | Kimble et al. | 5,486,627 A | 1/1996 | Quarderer et al. |
| 5,093,542 A | 3/1992 | Gaffney | 5,489,719 A | 2/1996 | Le et al. |
| 5,096,469 A | 3/1992 | Keefer | 5,489,727 A | 2/1996 | Randolph et al. |
| 5,097,083 A | 3/1992 | Stauffer | 5,500,297 A | 3/1996 | Thompson et al. |
| 5,099,084 A | 3/1992 | Stauffer | 5,510,525 A | 4/1996 | Sen et al. |
| 5,101,657 A | 4/1992 | Lahlouh et al. | 5,523,503 A | 6/1996 | Funk et al. |
| 5,105,045 A | 4/1992 | Kimble et al. | 5,525,230 A | 6/1996 | Wrigley et al. |
| 5,105,046 A | 4/1992 | Washecheck | 5,538,540 A | 7/1996 | Whitlock |

| | | | | | | |
|---|---|---|---|---|---|---|
| 5,563,313 | A | 10/1996 | Chung et al. | 6,169,218 B1 | 1/2001 | Hearn et al. |
| 5,565,092 | A | 10/1996 | Pannell et al. | 6,180,841 B1 | 1/2001 | Fatutto et al. |
| 5,565,616 | A | 10/1996 | Li et al. | 6,187,871 B1 | 2/2001 | Thompson et al. |
| 5,571,762 | A | 11/1996 | Clerici et al. | 6,187,983 B1 | 2/2001 | Sun |
| 5,571,885 | A | 11/1996 | Chung et al. | 6,203,712 B1 | 3/2001 | Bronner et al. |
| 5,599,381 | A | 2/1997 | Whitlock | 6,207,864 B1 | 3/2001 | Henningsen et al. |
| 5,600,043 | A | 2/1997 | Johnston et al. | 6,225,517 B1 | 5/2001 | Nascimento et al. |
| 5,600,045 | A | 2/1997 | Van Der Aalst et al. | 6,248,218 B1 | 6/2001 | Linkous et al. |
| 5,609,654 | A | 3/1997 | Le et al. | 6,265,505 B1 | 7/2001 | McConville et al. |
| 5,633,419 | A | 5/1997 | Spencer et al. | 6,281,405 B1 | 8/2001 | Davis et al. |
| 5,639,930 | A | 6/1997 | Penick | 6,320,085 B1 | 11/2001 | Arvai et al. |
| 5,653,956 | A | 8/1997 | Zones | 6,337,063 B1 | 1/2002 | Rouleau et al. |
| 5,656,149 | A | 8/1997 | Zones et al. | 6,337,309 B1 | 1/2002 | Watts |
| 5,661,097 | A | 8/1997 | Spencer et al. | 6,342,200 B1 | 1/2002 | Rouleau et al. |
| 5,663,465 | A | 9/1997 | Clegg et al. | 6,368,490 B1 | 4/2002 | Gestermann |
| 5,663,474 | A | 9/1997 | Pham et al. | 6,369,283 B1 | 4/2002 | Guram et al. |
| 5,675,046 | A | 10/1997 | Ohno et al. | 6,372,949 B1 | 4/2002 | Brown et al. |
| 5,675,052 | A | 10/1997 | Menon et al. | 6,376,731 B1 | 4/2002 | Evans et al. |
| 5,679,134 | A | 10/1997 | Brugerolle et al. | 6,380,328 B1 | 4/2002 | McConville et al. |
| 5,679,879 | A | 10/1997 | Mercier et al. | 6,380,423 B2 | 4/2002 | Banning et al. |
| 5,684,213 | A | 11/1997 | Nemphos et al. | 6,380,444 B1 | 4/2002 | Bjerrum et al. |
| 5,693,191 | A | 12/1997 | Pividal et al. | 6,395,945 B1 | 5/2002 | Randolph |
| 5,695,890 | A | 12/1997 | Thompson et al. | 6,403,840 B1 | 6/2002 | Zhou et al. |
| 5,698,747 | A | 12/1997 | Godwin et al. | 6,406,523 B1 | 6/2002 | Connor et al. |
| 5,705,712 | A | 1/1998 | Frey et al. | 6,423,211 B1 | 7/2002 | Randolph et al. |
| 5,705,728 | A | 1/1998 | Viswanathan et al. | 6,426,441 B1 | 7/2002 | Randolph et al. |
| 5,705,729 | A | 1/1998 | Huang | 6,426,442 B1 | 7/2002 | Ichikawa et al. |
| 5,708,246 | A | 1/1998 | Camaioni et al. | 6,452,058 B1 | 9/2002 | Schweizer et al. |
| 5,720,858 | A | 2/1998 | Noceti et al. | 6,455,650 B1 | 9/2002 | Lipian et al. |
| 5,728,897 | A | 3/1998 | Buysch et al. | 6,462,243 B1 | 10/2002 | Zhou et al. |
| 5,728,905 | A | 3/1998 | Clegg et al. | 6,465,696 B1 | 10/2002 | Zhou et al. |
| 5,734,073 | A | 3/1998 | Chambers et al. | 6,465,699 B1 | 10/2002 | Grosso |
| 5,741,949 | A | 4/1998 | Mack | 6,472,345 B2 | 10/2002 | Hintermann et al. |
| 5,744,669 | A | 4/1998 | Kalnes et al. | 6,472,572 B1 | 10/2002 | Zhou et al. |
| 5,750,801 | A | 5/1998 | Buysch et al. | 6,475,463 B1 | 11/2002 | Elomari et al. |
| 5,770,175 | A | 6/1998 | Zones | 6,475,464 B1 | 11/2002 | Rouleau et al. |
| 5,776,871 | A | 7/1998 | Cothran et al. | 6,479,705 B2 | 11/2002 | Murata et al. |
| 5,780,703 | A | 7/1998 | Chang et al. | 6,482,997 B2 | 11/2002 | Petit-Clair et al. |
| 5,798,314 | A | 8/1998 | Spencer et al. | 6,486,368 B1 | 11/2002 | Zhou et al. |
| 5,814,715 | A | 9/1998 | Chen et al. | 6,495,484 B1 | 12/2002 | Holtcamp |
| 5,817,904 | A | 10/1998 | Vic et al. | 6,509,485 B2 | 1/2003 | Mul et al. |
| 5,821,394 | A | 10/1998 | Schoebrechts et al. | 6,511,526 B2 | 1/2003 | Jagger et al. |
| 5,847,224 | A | 12/1998 | Koga et al. | 6,514,319 B2 | 2/2003 | Keefer et al. |
| 5,849,978 | A | 12/1998 | Benazzi et al. | 6,518,474 B1 | 2/2003 | Sanderson et al. |
| 5,866,735 | A | 2/1999 | Cheung et al. | 6,518,476 B1 | 2/2003 | Culp et al. |
| 5,895,831 | A | 4/1999 | Brasier et al. | 6,525,228 B2 | 2/2003 | Chauvin et al. |
| 5,898,086 | A | 4/1999 | Harris | 6,525,230 B2 | 2/2003 | Grosso |
| 5,905,169 | A | 5/1999 | Jacobson | 6,528,693 B1 | 3/2003 | Gandy et al. |
| 5,906,892 | A | 5/1999 | Thompson et al. | 6,538,162 B2 | 3/2003 | Chang et al. |
| 5,908,963 | A | 6/1999 | Voss et al. | 6,540,905 B1 | 4/2003 | Elomari |
| 5,952,538 | A | 9/1999 | Vaughn et al. | 6,545,191 B1 | 4/2003 | Stauffer |
| 5,959,170 | A | 9/1999 | Withers | 6,547,958 B1 | 4/2003 | Elomari |
| 5,968,236 | A | 10/1999 | Bassine | 6,548,040 B1 | 4/2003 | Rouleau et al. |
| 5,969,195 | A | 10/1999 | Stabel et al. | 6,552,241 B1 | 4/2003 | Randolph et al. |
| 5,977,402 | A | 11/1999 | Sekiguchi et al. | 6,566,572 B2 | 5/2003 | Okamoto et al. |
| 5,983,476 | A | 11/1999 | Eshelman et al. | 6,572,829 B2 | 6/2003 | Linkous et al. |
| 5,986,158 | A | 11/1999 | Van Broekhoven et al. | 6,585,953 B2 | 7/2003 | Roberts et al. |
| 5,994,604 | A | 11/1999 | Reagen et al. | 6,616,830 B2 | 9/2003 | Elomari |
| 5,998,679 | A | 12/1999 | Miller | 6,620,757 B2 | 9/2003 | McConville et al. |
| 5,998,686 | A | 12/1999 | Clem et al. | 6,632,971 B2 | 10/2003 | Brown et al. |
| 6,002,059 | A | 12/1999 | Hellring et al. | 6,635,793 B2 | 10/2003 | Mul et al. |
| 6,015,867 | A | 1/2000 | Fushimi et al. | 6,641,644 B2 | 11/2003 | Jagger et al. |
| 6,018,088 | A | 1/2000 | Olah | 6,646,102 B2 | 11/2003 | Boriack et al. |
| 6,022,929 | A | 2/2000 | Chen et al. | 6,669,846 B2 | 12/2003 | Perriello |
| 6,034,288 | A | 3/2000 | Scott et al. | 6,672,572 B2 | 1/2004 | Werlen |
| 6,056,804 | A | 5/2000 | Keefer et al. | 6,679,986 B1 | 1/2004 | Da Silva et al. |
| 6,068,679 | A | 5/2000 | Zheng | 6,680,415 B1 | 1/2004 | Gulotty, Jr. et al. |
| 6,072,091 | A | 6/2000 | Cosyns et al. | 6,692,626 B2 | 2/2004 | Keefer et al. |
| 6,087,294 | A | 7/2000 | Klabunde et al. | 6,692,723 B2 | 2/2004 | Rouleau et al. |
| 6,090,312 | A | 7/2000 | Ziaka et al. | 6,710,213 B2 | 3/2004 | Aoki et al. |
| 6,096,932 | A | 8/2000 | Subramanian | 6,713,087 B2 | 3/2004 | Tracy et al. |
| 6,096,933 | A | 8/2000 | Cheung et al. | 6,713,655 B2 | 3/2004 | Yilmaz et al. |
| 6,103,215 | A | 8/2000 | Zones et al. | RE38,493 E | 4/2004 | Keefer et al. |
| 6,107,561 | A | 8/2000 | Thompson | 6,723,808 B2 | 4/2004 | Holtcamp |
| 6,117,371 | A | 9/2000 | Mack | 6,727,400 B2 | 4/2004 | Messier et al. |
| 6,124,514 | A | 9/2000 | Emmrich et al. | 6,740,146 B2 | 5/2004 | Simonds |
| 6,127,588 | A | 10/2000 | Kimble et al. | 6,753,390 B2 | 6/2004 | Ehrman et al. |
| 6,130,260 | A | 10/2000 | Hall et al. | 6,765,120 B2 | 7/2004 | Weber et al. |
| 6,143,939 | A | 11/2000 | Farcasiu et al. | 6,797,845 B1 | 9/2004 | Hickman et al. |

| | | | | | | |
|---|---|---|---|---|---|---|
| 6,797,851 B2 | 9/2004 | Martens et al. | 7,253,327 B2 | 8/2007 | Janssens et al. | |
| 6,821,924 B2 | 11/2004 | Gulotty, Jr. et al. | 7,253,328 B2 | 8/2007 | Stauffer | |
| 6,822,123 B2 | 11/2004 | Stauffer | 7,265,193 B2 | 9/2007 | Weng et al. | |
| 6,822,125 B2 | 11/2004 | Lee et al. | 7,267,758 B2 | 9/2007 | Benazzi et al. | |
| 6,825,307 B2 | 11/2004 | Goodall | 7,268,263 B1 | 9/2007 | Frey et al. | |
| 6,825,383 B1 | 11/2004 | Dewkar et al. | 7,271,303 B1 | 9/2007 | Sechrist et al. | |
| 6,831,032 B2 | 12/2004 | Spaether | 7,273,957 B2 | 9/2007 | Bakshi et al. | |
| 6,838,576 B1 | 1/2005 | Wicki et al. | 7,282,603 B2 | 10/2007 | Richards | |
| 6,841,063 B2 | 1/2005 | Elomari | 7,285,698 B2 | 10/2007 | Liu et al. | |
| 6,852,896 B2 | 2/2005 | Stauffer | 7,304,193 B1 | 12/2007 | Frey et al. | |
| 6,866,950 B2 | 3/2005 | Connor et al. | 7,342,144 B2 | 3/2008 | Kaizik et al. | |
| 6,869,903 B2 | 3/2005 | Matsunaga | 7,348,295 B2 | 3/2008 | Zones et al. | |
| 6,875,339 B2 | 4/2005 | Rangarajan et al. | 7,348,464 B2 | 3/2008 | Waycuilis | |
| 6,878,853 B2 | 4/2005 | Tanaka et al. | 7,357,904 B2 | 4/2008 | Zones et al. | |
| 6,888,013 B2 | 5/2005 | Paparatto et al. | 7,361,794 B2 * | 4/2008 | Grosso | 568/891 |
| 6,900,363 B2 | 5/2005 | Harth et al. | 7,390,395 B2 | 6/2008 | Elomari | |
| 6,902,602 B2 | 6/2005 | Keefer et al. | 7,579,510 B2 * | 8/2009 | Gadewar et al. | 585/310 |
| 6,903,171 B2 | 6/2005 | Rhodes et al. | 7,674,941 B2 * | 3/2010 | Waycuilis et al. | 585/408 |
| 6,909,024 B1 | 6/2005 | Jones et al. | 7,812,201 B2 * | 10/2010 | Miller et al. | 568/891 |
| 6,921,597 B2 | 7/2005 | Keefer et al. | 2002/0102672 A1 | 8/2002 | Mizrahi | |
| 6,933,417 B1 | 8/2005 | Henley et al. | 2002/0198416 A1 | 12/2002 | Zhou et al. | |
| 6,946,566 B2 | 9/2005 | Yaegashi et al. | 2003/0004380 A1 | 1/2003 | Grumann | |
| 6,953,868 B2 | 10/2005 | Boaen et al. | 2003/0065239 A1 | 4/2003 | Zhu | |
| 6,953,873 B2 | 10/2005 | Cortright et al. | 2003/0069452 A1 | 4/2003 | Sherman et al. | |
| 6,956,140 B2 | 10/2005 | Ehrenfeld | 2003/0078456 A1 | 4/2003 | Yilmaz et al. | |
| 6,958,306 B2 | 10/2005 | Holtcamp | 2003/0120121 A1 | 6/2003 | Sherman et al. | |
| 6,984,763 B2 | 1/2006 | Schweizer et al. | 2003/0125589 A1 | 7/2003 | Grosso | |
| 7,001,872 B2 | 2/2006 | Pyecroft et al. | 2003/0166973 A1 | 9/2003 | Zhou et al. | |
| 7,002,050 B2 | 2/2006 | Santiago Fernandez et al. | 2004/0006246 A1 | 1/2004 | Sherman | |
| 7,011,811 B2 | 3/2006 | Elomari | 2004/0062705 A1 | 4/2004 | Leduc | |
| 7,019,182 B2 | 3/2006 | Grosso | 2004/0152929 A1 | 8/2004 | Clarke | |
| 7,026,145 B2 | 4/2006 | Mizrahi et al. | 2004/0158107 A1 | 8/2004 | Aoki | |
| 7,026,519 B2 | 4/2006 | Santiago Fernandez et al. | 2004/0158108 A1 | 8/2004 | Snoble | |
| 7,037,358 B2 | 5/2006 | Babicki et al. | 2004/0187684 A1 | 9/2004 | Elomari | |
| 7,045,670 B2 | 5/2006 | Johnson et al. | 2005/0038310 A1 | 2/2005 | Lorkovic et al. | |
| 7,049,388 B2 | 5/2006 | Boriack et al. | 2005/0047927 A1 | 3/2005 | Lee et al. | |
| 7,053,252 B2 | 5/2006 | Boussand et al. | 2005/0148805 A1 | 7/2005 | Jones | |
| 7,057,081 B2 | 6/2006 | Allison et al. | 2005/0171393 A1 | 8/2005 | Lorkovic | |
| 7,060,865 B2 | 6/2006 | Ding et al. | 2005/0192468 A1 | 9/2005 | Sherman et al. | |
| 7,064,238 B2 | 6/2006 | Waycuilis | 2005/0215837 A1 | 9/2005 | Hoffpauir | |
| 7,064,240 B2 | 6/2006 | Ohno et al. | 2005/0234276 A1 | 10/2005 | Waycuilis | |
| 7,067,448 B1 | 6/2006 | Weitkamp et al. | 2005/0245772 A1 | 11/2005 | Fong | |
| 7,083,714 B2 | 8/2006 | Elomari | 2005/0245777 A1 | 11/2005 | Fong | |
| 7,084,308 B1 | 8/2006 | Stauffer | 2005/0267224 A1 | 12/2005 | Herling | |
| 7,091,270 B2 | 8/2006 | Zilberman et al. | 2006/0025617 A1 | 2/2006 | Begley | |
| 7,091,387 B2 | 8/2006 | Fong et al. | 2006/0100469 A1 | 5/2006 | Waycuilis | |
| 7,091,391 B2 | 8/2006 | Stauffer | 2006/0135823 A1 | 6/2006 | Jun | |
| 7,094,936 B1 | 8/2006 | Owens et al. | 2006/0138025 A1 | 6/2006 | Zones | |
| 7,098,371 B2 | 8/2006 | Mack et al. | 2006/0138026 A1 | 6/2006 | Chen | |
| 7,105,710 B2 | 9/2006 | Boons et al. | 2006/0149116 A1 | 7/2006 | Slaugh | |
| 7,138,534 B2 | 11/2006 | Forlin et al. | 2006/0229228 A1 | 10/2006 | Komon et al. | |
| 7,141,708 B2 | 11/2006 | Marsella et al. | 2006/0229475 A1 | 10/2006 | Weiss et al. | |
| 7,145,045 B2 | 12/2006 | Harmsen et al. | 2006/0270863 A1 | 11/2006 | Reiling | |
| 7,148,356 B2 | 12/2006 | Smith, III et al. | 2006/0288690 A1 | 12/2006 | Elomari | |
| 7,148,390 B2 | 12/2006 | Zhou et al. | 2007/0004955 A1 | 1/2007 | Kay | |
| 7,151,199 B2 | 12/2006 | Martens et al. | 2007/0078285 A1 | 4/2007 | Dagle | |
| 7,161,050 B2 | 1/2007 | Sherman et al. | 2007/0100189 A1 | 5/2007 | Stauffer | |
| 7,169,730 B2 | 1/2007 | Ma et al. | 2007/0129584 A1 | 6/2007 | Basset | |
| 7,176,340 B2 | 2/2007 | Van Broekhoven et al. | 2007/0142680 A1 | 6/2007 | Ayoub | |
| 7,176,342 B2 | 2/2007 | Bellussi et al. | 2007/0148067 A1 | 6/2007 | Zones | |
| 7,182,871 B2 | 2/2007 | Perriello | 2007/0148086 A1 | 6/2007 | Zones | |
| 7,193,093 B2 | 3/2007 | Murray et al. | 2007/0149778 A1 | 6/2007 | Zones | |
| 7,196,239 B2 | 3/2007 | Van Egmond et al. | 2007/0149789 A1 | 6/2007 | Zones | |
| 7,199,083 B2 | 4/2007 | Zevallos | 2007/0149819 A1 | 6/2007 | Zones | |
| 7,199,255 B2 | 4/2007 | Murray et al. | 2007/0149824 A1 | 6/2007 | Zones | |
| 7,208,641 B2 | 4/2007 | Nagasaki et al. | 2007/0149837 A1 | 6/2007 | Zones | |
| 7,214,750 B2 | 5/2007 | McDonald et al. | 2007/0197801 A1 | 8/2007 | Bolk | |
| 7,220,391 B1 | 5/2007 | Huang et al. | 2007/0197847 A1 | 8/2007 | Liu | |
| 7,226,569 B2 | 6/2007 | Elomari | 2007/0213545 A1 | 9/2007 | Bolk | |
| 7,226,576 B2 | 6/2007 | Elomari | 2007/0238905 A1 | 10/2007 | Arredondo | |
| 7,230,150 B2 * | 6/2007 | Grosso et al. ............ 585/323 | 2007/0238909 A1 | 10/2007 | Gadewar et al. | |
| 7,230,151 B2 | 6/2007 | Martens et al. | 2007/0251382 A1 | 11/2007 | Gadewar | |
| 7,232,872 B2 | 6/2007 | Shaffer et al. | 2007/0276168 A1 | 11/2007 | Garel | |
| 7,238,846 B2 | 7/2007 | Janssen et al. | 2007/0284284 A1 | 12/2007 | Zones | |
| 7,244,795 B2 | 7/2007 | Agapiou et al. | 2008/0171898 A1 | 7/2008 | Waycuilis | |
| 7,244,867 B2 | 7/2007 | Waycuilis | 2008/0183022 A1 | 7/2008 | Waycuilis | |
| 7,250,107 B2 | 7/2007 | Benazzi et al. | 2008/0188697 A1 | 8/2008 | Lorkovic | |
| 7,250,542 B2 | 7/2007 | Smith, Jr. et al. | 2008/0269534 A1 | 10/2008 | Lorkovic | |
| 7,252,920 B2 | 8/2007 | Kurokawa et al. | 2008/0314758 A1 | 12/2008 | Grosso | |

| | | | |
|---|---|---|---|
| 2009/0069606 A1 | 3/2009 | Komon | |
| 2010/0096588 A1 | 4/2010 | Gadewar | |
| 2010/0099928 A1 | 4/2010 | Gadewar | |
| 2010/0099929 A1 | 4/2010 | Gadewar | |
| 2010/0099930 A1 | 4/2010 | Stoimenov | |
| 2010/0105972 A1 | 4/2010 | Lorkovic | |
| 2010/0121119 A1 | 5/2010 | Sherman | |

FOREIGN PATENT DOCUMENTS

| | | |
|---|---|---|
| CA | 1099656 | 4/1981 |
| CA | 1101441 | 5/1981 |
| CA | 1202610 | 4/1986 |
| CA | 2447761 A1 | 11/2002 |
| CA | 2471295 A1 | 7/2003 |
| CA | 2542857 | 5/2005 |
| CA | 2236126 | 8/2006 |
| CA | 2203115 | 9/2006 |
| CA | 2510093 | 12/2006 |
| EP | 0021497 | 1/1981 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 7/1998 |
| EP | 1186591 A2 | 3/2002 |
| EP | 1253126 A1 | 10/2002 |
| EP | 1312411 A2 | 5/2003 |
| EP | 1395536 | 3/2004 |
| EP | 1404636 | 4/2004 |
| EP | 1235769 B1 | 5/2004 |
| EP | 1435349 A2 | 7/2004 |
| EP | 1440939 A1 | 7/2004 |
| EP | 1474371 | 11/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 2/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 | 11/1961 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 A | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| JP | 2004-529189 | 9/2004 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006-067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A1 | 8/2006 |
| WO | 2006-100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |

| | | | |
|---|---|---|---|
| WO | 2007/050745 A1 | 5/2007 | |
| WO | 2007/071046 A1 | 6/2007 | |
| WO | 2007/079038 A2 | 7/2007 | |
| WO | 2007/091009 A2 | 8/2007 | |
| WO | 2007/094995 A2 | 8/2007 | |
| WO | 2007/107031 A1 | 9/2007 | |
| WO | 2007/111997 A2 | 10/2007 | |
| WO | 2007/114479 A1 | 10/2007 | |
| WO | 2007/125332 A1 | 11/2007 | |
| WO | 2007/130054 A1 | 11/2007 | |
| WO | 2007/130055 A1 | 11/2007 | |
| WO | 2007/141295 A1 | 12/2007 | |
| WO | 2007/142745 A1 | 12/2007 | |
| WO | 2008/036562 | 3/2008 | |
| WO | 2008/036563 | 3/2008 | |
| WO | 2008/106319 | 9/2008 | |
| WO | 2008/148113 | 12/2008 | |
| WO | 2008/157043 | 12/2008 | |
| WO | 2008/157044 | 12/2008 | |
| WO | 2008/157045 | 12/2008 | |
| WO | 2008/157046 | 12/2008 | |
| WO | 2008/157047 | 12/2008 | |

OTHER PUBLICATIONS

U.S. Appl. No. 60/559,844, filed Apr. 6, 2004, Sherman et al.
U.S. Appl. No. 60/765,115, filed Feb. 3, 2006, Gadewar et al.
Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP2007061594, Method for decomposing organohalogen compound and mobile decomposition system, Publication date: Mar. 15, 2007, Inventor: Koichi et al., esp@cenet database—worldwide.
Abstract of JP2007099729, Method for producing alpha-methylstyrene or cumene, Publication date: Apr. 19, 2007, Inventor: Toshio, esp@cenet database—worldwide.
Abstract of RO119778, Process for preparing perchloroethylene, Publication date: Mar. 30, 2005, Inventor: Horia et al., esp@cenet database—worldwide.
Abstract of WO0105737, Method for preparing a carboxylic acid, Publication date: Jan. 25, 2001, Inventor: Pascal et al., esp@cenet database—worldwide.
Abstract of WO0105738, Method for preparing a carboxylic acid, Publication date: Jan. 25, 2001, Inventor: Pascal et al., esp@cenet database—worldwide.
Abstract of WO2004092099, Method for producing cyclic enols, Publication date: Oct. 28, 2004, Inventor: Marko et al., esp@cenet database—worldwide.
Abstract of WO2006063852, Electroluminescent polymers and use thereof, Publication date: Jun. 22, 2006, Inventor: Arne et al., esp@cenet database—worldwide.
Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO2007028761, Method for chlorinating alcohols, Publication date: Mar. 15, 2007, Inventor: Rohde et al., esp@cenet database—worldwide.
Abstract of WO2007128842, Catalytic transalkylation of dialkyl benzenes, Publication date: Nov. 15, 2007, Inventor: Goncalvesalmeida et al., esp@cenet database—worldwide.
Abstract of WO2007137566, Method for catalytic conversion of organic oxygenated compounds from biomaterials, Publication date: Dec. 19, 1997, Inventor: Reschetilowski, esp@cenet database—worldwide.
Abstract of WO9721656, Method for making fluoroalkanols, Publication date: Jun. 19, 1997, Inventor: Gillet, esp@cenet database—worldwide.
Abstract of WO9950213, Method for producing dialkyl ethers, Publication date: Oct. 7, 1999, Inventor: Falkowski Juergen et al., esp@cenet database—worldwide.
Adachi, et al.; Synthesis of Sialyl Lewis X Ganglioside Analogs Containing a Variable Length Spacer Between the Sugar and Lipophilic Moieties; J. Carbohydrate Chem., vol. 17, No. 4-5, (1998), pp. 595-607, XP009081720.

Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.
Abstract of EP0101337, Process for the production of methylene chloride, Publication date: Feb. 22, 1984, Inventor: Olah et al., esp@cenet database—worldwide.
Abstract of EP0407989, Method for the production of 1,1,1-trifluoro-2,2-dichloroethane by photochlorination, Publication date: Jan. 16, 1991, Inventor: Cremer et al., esp@cenet database—worldwide.
Abstract of EP0442258, Process for the preparation of a polyunsaturated olefin, Publication date: Aug. 21, 1991, Inventor: Gaudin et al., esp@cenet database—worldwide.
Abstract of EP0465294, Process for the preparation of unsaturated bromides, Publication date: Jan. 8, 1992, Inventor: Decaudin et al., esp@cenet database—worldwide.
Abstract of EP0549387, Synthesis of n-perfluorooctylbromide, Publication date: Jun. 30, 1993, Inventor: Drivon et al. al., esp@cenet database—worldwide.
Abstract of EP0850906, Process and apparatus for the etherification of olefinic hydrocarbon feedstocks, Publication date: Jul. 1, 1998, Inventor: Masson, esp@cenet database—worldwide.
Abstract of EP0858987, Process for the conversion of lighter alkanes to higher hydrocarbons, Publication date: Aug. 19, 1998, Inventor: Amariglio et al., esp@cenet database—worldwide.
Bakker, et al.; An Exploratory Study of the Addition Reaction of Ethyleneglcol, 2-Chloroethanlo and 1, 3-Dichloro-2-Propanol to 1-Dodecene; J. Am. Oil Chem. Soc., vol. 44, No. 9 (1967), pp. 517-521; XP009081570.
Abstract of EP0235110, Process for the stabilization of silicalite catalysts, Publication date: Sep. 2, 1987, Inventor: Debras et al., esp@cenet database—worldwide.
Bouzide et al.; Highly Selective Silver (I) Oxide Mediated Monoprotection of Symmetricl Diols; Tetrahedron Letters, Elsevier, vol. 38, No. 34 (1997), pp. 5945-5948; XP004094157.
Combined International Search Report and Written Opinion Dated Apr. 17, 2007 for PCT/US06/13394, in the name of GRT, Inc.
Gibson; Phase-Transfer Synthesis of Monoalkyl Ethers of Oligoethylene Glycols; Journal of Organic Chemistry, vol. 45, No. 6 (1980) pp. 1095-1098; XP002427776.
Klabunde, Kenneth J., et al., Changes in Texture and Catalytic Activity of Nanocrystalline MgO during Its Transformation to MgC12 in the Reaction with 1-Chlorobutane, J. Phys. Chem. B 2001, 105, 3937-3941. cited by other.
Loiseau et al.; Multigram Synthesis of Well-Defined Extended Bifunctional Polyethylene Glycol (PEG) Chains; J. of Organic Chem., vol. 69, No. 3 (2004), pp. 639-647; XP002345040.
Mihai et al.; Application of Bronsted-type LFER in the study of phospholipase C mechanism; J. Am. Chem. Soc., vol. 125, No. 11 (2003) pp. 3236-3242; XP002427799.
Motupally et al., Recycling Chlorine from Hydrogen Chloride: A New and Economical Electrolytic Process, The Electrochemical Society Interface, Fall 1998.
Nishikawa et al.; Ultrasonic Relaxations in Aqueous Solutions of Alcohols and the Balance Between Hydrophobicity and Hydrophilicity of the Solutes; J. Phys. Chem. vol. 97, No. 14 (1993), pp. 3539-3544; XP002427775.
Prelog et al.; Chirale 2,2'-Polyoxaalkano-9,9'-Spirobifluorene; Helvetica Chimica ACTA, vol. 62, No. 7, (1979) pp. 2285-2302; XP002030901.
Shimizu et al., Gas-Phase Electrolysis of Hydrobromic Acid Using PTFE-Bonded Carbon Eletrode, Int. J. Hydrogen Energy, vol. 13, No. 6. pp. 345-349, 1988.
Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.
Whitesides et al.; Nuclear Magnetic Resonance Spectroscopy. The Effect of Structure on Magnetic Nonequivalence Due to Molecular Asymmetry; J. Am. Chem. Soc., vol. 86, No. 13 (1964), pp. 2628-2634; XP002427774.
JLM Technology Ltd.; "The Miller GLS Technology for Conversion of Light Hydrocarbons to Alcohols"; New Science for the Benefit of Humanity; May 31, 2000; pp. 1-10.

Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.
Taylor, Charles E.; "Conversion of Substituted Methanes Over ZSM-Catalysts"; 2000; pp. 3633-3638; Studies in Surface Science and Catalysis 130; Elsevier Science B.V.
ZSM-5 Catalyst; http://chemelab.ucsd.edu/methanol/memos/ZSM-5.html; Nov. 6, 2003; p. 1.
Final Report; "Abstract"; http://chemelab.ucsd.edu/methanol/memos/final.html; May 9, 2004; pp. 1-7.
Driscoll, Daniel J.; "Direct Methane Conversion"; Federal Energy Technology Center, U.S. Department of Energy; M970779; 2001; pp. 1-10.
Olah et al.; "Selective Monohalogenation of Methane over Supported Acid or Platinum Metal Catalysts and Hydrolysis of Methyl Halides . . ."; J. American Chemical Society 1985, vol. 107; 0002-7863/85/1507-7097$01.50/0; pp. 7097-7105.
Murray et al.; "Conversion of Methyl Halides to Hydrocarbons on Basic Zeolites: A Discovery by in Situ NMR"; J. American Chemical Society 1993, vol. 115; pp. 4732-4741.
Lorkovic et al.; "A Novel Integrated Process for the Functionalization of Methane and Ethane: Bromine as Mediator", Catalysis Today 98; 2004; pp. 317-322.
Lorkovic et al.; "C1 Oxidative Coupling via Bromine Activation and Tandem Catalytic Condensation over CaO/Zeolite Composites II . . ."; Catalysis Today 98; 2004; pp. 589-594.
Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.
Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.
Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.
Zhou, Xiao-Ping et al.; "An Integrated Process for Partial Oxidation of Alkanes"; Chem. Commun. 2003; The Royal Society of Chemistry 2003; pp. 2294-2295.
Sun, Shouli et al.; "A General Integrated Process for Synthesizing Olefin Oxides"; Chem. Commun. 2004; The Royal Society of Chemistry 2004; pp. 2100-2101.
Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.
Yilmaz, Aysen et al.; "Bromine Mediated Partial Oxidation of Ethane over Nanostructured Zirconia Supported Metal Oxide/Bromide"; Microporous and Mesporous Materials, 79; 2005; pp. 205-214.
Taylor, Charles E.; "PETC's On-Site Natural Gas Conversion Efforts"; Preprints of the Fuel Division, 208th National Meeting of the American Chemical Society, 39 (4); 1994; pp. 1228-1232.
Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.
Olah, George A. et al.; "Hydrocarbons Through Methane Derivatives"; Hydrocarbon Chemistry; 1995; pp. 89-90; John Wiley & Sons, Inc.
Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions";.Tetrahedron Letters, vol. 36, No. 51, 1995; pp. 9365-9368; Pergamon; Great Britain.
Smirnov, Vladimir V. et al.; "Selective Bromination of Alkanes and Arylalkanes with CBr4"; Mendeleev Commun. 2000; pp. 175-176.
Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.
Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.
Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.
Mochida, Isao et al.; "The Catalytic Dehydrohalogenation of Haloethanes on Solid Acids and Bases"; Bulletin of the Chemical Society of Japan, vol. 44; 1971; pp. 3305-3310.
Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.
Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.
Mishakov, Ilya V. et al.; "Nanocrystalline MgO as a Dehydrohalogenation Catalyst"; Journal of Catalysis 206; 2002; pp. 40-48; Elsevier Science, USA.
Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.
Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.
http://webbook.nist.govi; "Welcome to the NIST Chemistry WebBook"; 2005; U.S. Secretary of Commerce on Behalf of the United States of America.
Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.
Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.
Thomas, John Meurig et al.; "Catalytically Active Centres in Porous Oxides: Design and Performance of Highly Selective New Catalysts"; Chem. Commun.; 2001; pp. 675-687.
Lorkovic, Ivan et al.; "C1 Coupling via Bromine Activation and Tandem Catalytic Condensation and Neutralization over CaO/Zeolite Composites"; Chem. Commun., 2004; pp. 566-567.
Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.
Weissermel, Klaus et al.; "Industrial Organic Chemistry"; 3rd Edition 1997. pp. 160-162, and 208.
Abstract of BE812868, Aromatic hydrocarbons prodn. from chlorinated hydrocarbons, Publication date: Sep. 27, 1974, esp@cenet database—worldwide.
Abstract of BE814900, Volatile aramatic cpds. prodn., Publication date: Sep. 2, 1974, esp@cenet database—worldwide.
Abstract of CN1199039, Pentanol and its production process, Publication date: Nov. 18, 1998, Inventor: Kailun, esp@cenet database—worldwide.
Abstract of CN1210847, Process for producing low carbon alcohol by directly hydrating low carbon olefines, Publication date: Mar. 17, 1999, Inventor: Zhenguo et al., esp@cenet database—worldwide.
Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.
Abstract of CN1623969, Method for preparing 1, 4-benzene dimethanol, Publication date: Jun. 8, 2005, Inventor: Jiarong et al., esp@cenet database—worldwide.
Abstract of CN1657592, Method for converting oil to multiple energy fuel product, Publication date: Aug. 24, 2005, Inventor: Li, esp@cenet database—worldwide.
Abstract of CN1687316, Method for producing biologic diesel oil from rosin, Publication date: Oct. 26, 2005, Inventor: Jianchun et al., esp@cenet database—worldwide.
Abstract of CN1696248, Method for synthesizing biologic diesel oil based on ion liquid, Publication date: Nov. 16, 2005, Inventor: Sun, esp@cenet database—worldwide.
Abstract of CN1699516, Process for preparing bio-diesel-oil by using microalgae fat, Publication date: Nov. 23, 2005, Inventor: Miao, esp@cenet database—worldwide.
Abstract of CN1704392, Process for producing alkylbenzene, Publication date: Dec. 7, 2005, Inventor: Gao, esp@cenet database—worldwide.
Abstract of CN1724612, Biological diesel oil catalyst and method of synthesizing biological diesel oil using sai catalyst, Publication date: Jan. 25, 2006, Inventor: Gu, esp@cenet database—worldwide.
Abstract of CN1986737, Process of producing biodiesel oil with catering waste oil, Publication date: Jun. 27, 2007, Inventor: Chen, esp@cenet database—worldwide.
Abstract of CN100999680, Esterification reaction tech. of preparing biodiesel by waste oil, Publication date: Jun. 18, 2007, Inventor: Weiming, esp@cenet database—worldwide.
Abstract of CN101016229, Refining method for bromomeoamyl alcohol, Publication date: Aug. 8, 2007, Inventor: Tian, esp@cenet database—worldwide.
Abstract of DE3209964, Process for the preparation of chlorinated hydrocarbons, Publication date: Nov. 11, 1982, Inventor: Pyke et al., esp@cenet database—worldwide.
Abstract of DE3210196, Process for the preparation of a monochlorinated olefin, Publication date: Jan. 5, 1983, Inventor: Pyke et al., esp@cenet database—worldwide.
Abstract of DE3226028, Process for the preparation of monochlorinated olefin, Publication date: Feb. 3, 1983, Inventor: Pyke et al., esp@cenet database—worldwide.
Abstract of DE3334225, Process for the preparation of 1, 2-dichloroethane, Publication date: Apr. 4, 1985, Inventor: Hebgen et al., esp@cenet database—worldwide.
Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE4434823, Continuous prodn. of hydroxy-benzyl alkyl ether, Publication date: Apr. 4, 1996, Inventor: Stein et al., esp@cenet database—worldwide.
Abstract of FR2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2-dichloroethane from reactor, Publication date: Oct. 6, 2006, Inventor: Balthasart et al., esp@cenet database—worldwide.
Abstract of IT1255246, Process for the preparation of dinitrodiphenylmethanes, Publication date: Oct. 20, 1995, Applicant: Enichem Spa et al., esp@cenet database—worldwide.
Abstract of IT1255358, Process for the synthesis of 1, 4-butanediol, Publication date: Oct. 31, 1995 Inventor: Marco, esp@cenet database—worldwide.
Abstract of JP2142740, Production of fluoroalcohol, Publication date: May 31, 1990, Inventor: Tsutomu et al., esp@cenet database—worldwide.
Abstract of JP2144150, Chemical process and catalyst used therefore, Publication date: Jun. 1, 1990, Inventor: Deidamusu et al., esp@cenet database—worldwide.
Abstract of JP4305542, Production of halogenated hydrocarbon compounds, Publication date: Oct. 28, 1992, Inventor: Shinsuke et al., esp@cenet database—worldwide.
Abstract of JP6172225, Method for fluorinating halogenated hydrocarbon, Publication date: Jun. 21, 1994, Inventor: or:Takashi et al., esp@cenet database—worldwide.
Abstract of JP6206834, Production of tetrachloroethanes, Publication date: Jul. 26, 1994, Inventor: Toshiro et al., esp@cenet database—worldwide.
Abstract of JP8266888, Method for decomposing aromatic halogen compound, Publication date: Oct. 15, 1996, Inventor: Yuuji et al., esp@cenet database—worldwide.
Abstract of JP2001031605, Production of 3-hydroxy-1-cycloalkene, Publication date: Feb. 6, 2001, Inventor: Hideo et al, esp@cenet database—worldwide.
Abstract of JP2004075683, Method for producing optically active halogenohydroxypropyl compound and glycidyl compound, Publication date: Mar. 11, 2004, Inventor: Keisuke et al., esp@cenet database—worldwide.
Abstract of JP2004189655, Method for fluorinating with microwave, Publication date: Jul. 8, 2004, Inventor: Masaharu et al., esp@cenet database—worldwide.
Abstract of JP2005075798, Method for Producing adamantyl ester compound, Publication date: Mar. 24, 2005, Inventor: Norihiro et al., esp@cenet database—worldwide.
Abstract of JP2005082563, Method for producing 1, 3-adamantanediol, Publication date: Mar. 31, 2005, Inventor: Norihiro et al., esp@cenet database—worldwide.
Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP2005254092, Method of manufacturing alkynes, Publication date: Sep. 22, 2005, Inventor: Shirakawa Eiji, esp@cenet database—worldwide.
Abstract of JP2006151892, Preparation method of alcohol derivative, Publication date: Jun. 15, 2006, Inventor: Baba Akio et al., esp@cenet database—worldwide.
Abstract of JP2006152263, Organic-inorganic hybrid-type mesoporous material, method for producing the same, and solid catalyst, Publication date: Jun. 15, 2006, Inventor: Junko et al., esp@cenet database—worldwide.
Abstract of JP2006193473, Aryl polyadamantane derivative having carboxy or acid anhydride group and method for producing the same, Publication date: Jul. 27, 2006, Inventor: Yasuto et al., esp@cenet database—worldwide.
Abstract of JP2006231318, Phosphorus containing macromolecule immobilizing palladium catalyst and method for using the same, Publication date: Sep. 7, 2006, Inventor: Osamu et al., esp@cenet database—worldwide.
Abstract of JP2006263567, Optical resolution method of optical isomer and optical resolution device, Publication date: Oct. 5, 2006, Inventor: Yoshikazu et al., esp@cenet database—worldwide.
Abstract of JP2006265157, Method for catalytically activating silicated nucleating agent using phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 1, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 1, 2007.

U.S. Office Action from U.S. Appl. No. 10/893,418 dated Jan. 2, 2008.

U.S. Office Action from U.S. Appl. No. 10/893,418 dated Jun. 14, 2007.

U.S. Office Action from U.S. Appl. No. 11/091,130 dated Oct. 3, 2007.

U.S. Office Action from U.S. Appl. No. 10/365,346 dated Jun. 12, 2006.

U.S. Office Action from U.S. Appl. No. 11/103,326 dated Aug. 31, 2007.

U.S. Office Action from U.S. Appl. No. 11/103,326 dated Dec. 6, 2006.

U.S. Office Action from U.S. Appl. No. 11/098,997 dated Nov. 20, 2008.

U.S. Office Action from U.S. Appl. No. 12/215,326 dated Feb. 10, 2009.

U.S. Office Action from U.S. Appl. No. 10/430,240 dated Mar. 6, 2006.

U.S. Office Action from U.S. Appl. No. 10/369,148 dated Oct. 16, 2006.

U.S. Office Action from U.S. Appl. No. 10/369,148 dated Mar. 14, 2006.

U.S. Office Action from U.S. Appl. No. 10/894,165 dated Aug. 16, 2006.

U.S. Office Action from U.S. Appl. No. 12/080,594 dated Dec. 22, 2008.

U.S. Office Action from U.S. Appl. No. 11/703,358 dated Jun. 11, 2008.

International Search Report for PCT/US08/64922 dated Oct. 13, 2008.

* cited by examiner

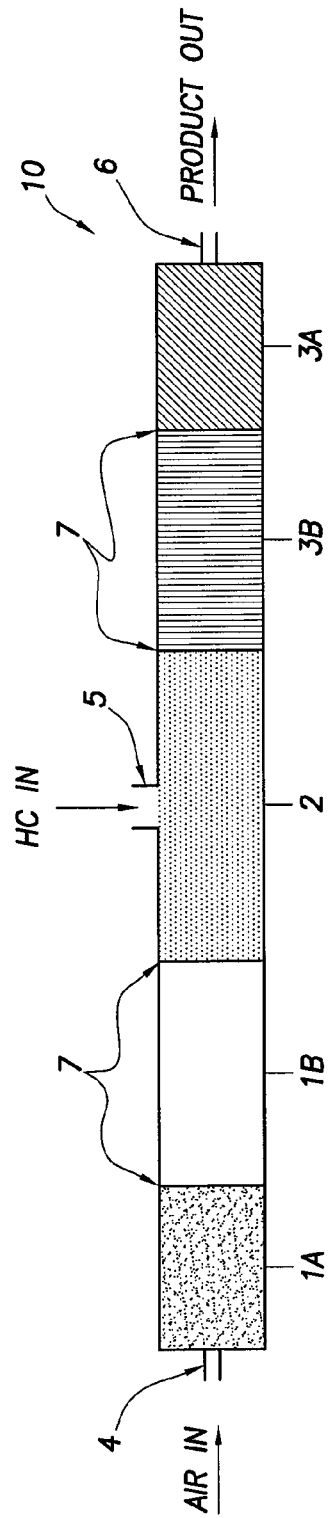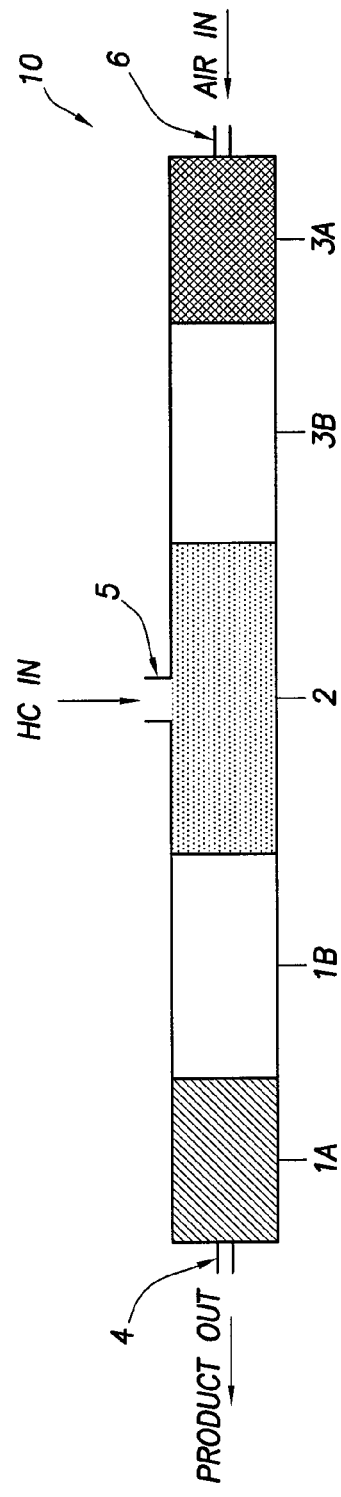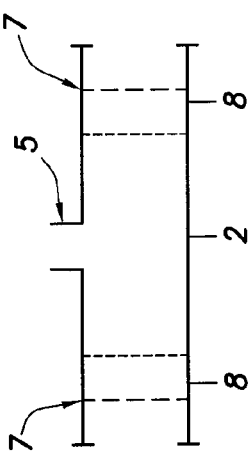

ZONE REACTOR INCORPORATING REVERSIBLE HYDROGEN HALIDE CAPTURE AND RELEASE

CROSS REFERENCE TO RELATED APPLICATION

This application claims the benefit of U.S. Provisional Application No. 60/931,891, filed May 24, 2007, the entire contents of which are incorporated by reference herein.

FIELD OF THE INVENTION

This invention relates to a process and apparatus for converting hydrocarbon feedstocks into higher hydrocarbons.

BACKGROUND OF THE INVENTION

U.S. Pat. No. 6,525,230 discloses a method of converting alkanes to alcohols and/or ethers, and a zone reactor comprised of a hollow, unsegregated interior defining first, second, and third zones. In a first embodiment, air or oxygen reacts with metal bromide in the first zone to provide bromine; bromine reacts with alkane(s) in the second zone to form alkyl bromides; and the alkyl bromides react with metal oxide in the third zone to form the corresponding product(s). Metal bromide from the third zone is transported through the vessel to the first zone, and metal oxide from the first zone is recycled to the third zone. A second embodiment differs from the first embodiment in that metal oxide is transported through the vessel from the first zone to the third zone, and metal bromide is recycled from the third zone to the first zone. In a third embodiment, the flow of gases through the vessel is reversed to convert the metal oxide back to metal bromide and to convert the metal bromide back to the metal oxide.

SUMMARY OF THE INVENTION

The present invention provides an improved zone reactor and a process for converting a hydrocarbon feedstock into one or more higher hydrocarbons. In one embodiment, an improved zone reactor comprises a vessel having first, second, and third zones, wherein the first zone contains both a material capable of releasing hydrogen halide (HX) and a carbon-carbon coupling catalyst; the second zone is initially empty (other than an ambient atmosphere) or contains a halogenation and/or oxyhalogenation catalyst; and the third zone contains both a carbon-carbon coupling catalyst and a material capable of capturing HX. Gases can flow through each of the first, second, and third zones. Preferably a gas inlet and/or outlet is provided in each of the first, second, and third zones, including an inlet in zone 2 for introducing a gaseous hydrocarbon feedstock.

In another aspect of the invention, an improved process for converting a hydrocarbon feedstock into higher hydrocarbons comprises forming HX by heating a material capable of releasing HX, in the presence of air or oxygen; optionally decoking a carbon-carbon coupling catalyst; forming alkyl halides by reacting a hydrocarbon feedstock with HX in the presence of air or oxygen; forming higher hydrocarbons and HX (and, less desirably, coke) by reacting the alkyl halides in the presence of a carbon-carbon coupling catalyst; and capturing HX by reacting it with a material capable of capturing HX. Preferably, the process is repeated multiple times, with alternating HX release and capture and alternating coking and decoking of the coupling catalyst. In one embodiment, HX is released by dehydrohalogenating a partially halogenated olefin or polyolefin, and captured by hydrohalogenating the olefin or polyolefin.

BRIEF DESCRIPTION OF THE DRAWINGS

These and other aspects and features of the invention will become more clear when considering in light of the appended drawings, wherein:

FIG. 1 is a schematic diagram of a zone reactor according to one embodiment of the invention; and FIG. 2 is a schematic diagram of zone 2 of an improved zone reactor according to another embodiment to the present invention.

DETAILED DESCRIPTION OF THE INVENTION

The present invention provides a process and an improved zone reactor for converting a hydrocarbon feedstock into one or more useful products, i.e., "higher hydrocarbons." Generally, the process comprises forming a first stream or quantity of hydrogen halide (HX) by heating a material capable of releasing HX in air or oxygen; forming alkyl halides by reacting a hydrocarbon feedstock and the first stream of HX in air or oxygen; forming higher hydrocarbons and a second stream or quantity of HX by reacting the alkyl halides in the presence of a second carbon-carbon coupling catalyst; and capturing the second stream of HX by reacting it with a material capable of capturing HX.

The general features and mode of operation of one embodiment of an improved zone reactor are schematically depicted in FIGS. 1A and 1B. A zone reactor 10 in the form of a generally hollow vessel contains a first zone 1 which is further subdivided into two subzones, 1A and 1B; a second zone 2; and a third zone 3, which is further subdivided into zones 3A and 3B.

Initially, zone 1A contains a material capable of releasing HX, as described below. Zone 1B contains a carbon-carbon coupling catalyst, which catalyzes carbon-carbon bond formation and the generation of higher hydrocarbons. Although not bound by theory, it is believed that carbon-carbon bond formation proceeds via intermolecular—and possibly even intramolecular—metathesis reactions of alkyl halide molecules. In the drawing, the catalyst in zone 1B is also coated and/or impregnated with coke, as described below. When the reactor is loaded for its inaugural run, however, no coke is present. Zone 2 is either empty or contains a halogenation and/or oxyhalogenation catalyst or cataloreactant. Zone 3B also contains a carbon-carbon coupling catalyst, and zone 3A contains a material capable of capturing HX.

A first opening or inlet 4 in the left end of the reactor allows air or oxygen to be introduced into the vessel. A second opening or inlet 5 in the middle of the reactor allows a gaseous hydrocarbon feedstock to be introduced, and a third opening or inlet 6, in the right end of the vessel allows product(s) to be withdrawn. In addition, each of the zones and subzones meet at boundaries 7 that permit the flow of gases into adjoining zones. In one embodiment, the vessel has an unsegregated interior, and adjacent zones and subzones are not physically separated from one another. In another embodiment, adjacent zones and subzones are separated by a screen, or by a wall or other divider that has at least one opening provided therein to permit gases to flow from one zone or subzone to the next. Various heaters and/or coolers (not shown) are thermally coupled to the vessel, directly or indirectly, to facilitate temperature control at each zone and subzone.

As shown in FIG. 1A, initially the reactor operates from left to right, with air or oxygen being introduced through a gas inlet 4 into zone 1A, causing the material contained therein to release gaseous HX. Heated air or oxygen and HX from zone 1A pass into zone 1B and into contact with the carbon-carbon coupling catalyst. The air or oxygen reacts with any coke that has previously been deposited in or on the catalyst and converts it to $CO_2$. In the presence of an excess of air or oxygen, any CO that is formed will also be converted to $CO_2$.

In zone 2, a gaseous, hydrocarbon feedstock is introduced into the vessel through the second gas inlet 5 and allowed to react with HX in the presence of air or oxygen and, preferably, a halogenation and/or oxyhalogenation catalyst or cataloreactant. This results in the formation of one or more alkyl halides (RX) and steam, which are carried, along with any HX that is present, into zone 3B. There, the alkyl halide(s) react in the presence of a carbon-carbon coupling catalyst and are converted to higher hydrocarbons and HX. The reaction also can, and typically will, result in the formation of coke, with coke particles being deposited on the carbon-carbon coupling catalyst as a coating and/or within the interstitial voids of the catalyst. The HX that is formed then reacts with a material capable of capturing it in zone 3A. The gaseous hydrocarbon products, $CO_2$, residual air (or its oxygen-depleted components), water, and possibly other species, are carried out of the reactor vessel through the third opening 6 and can be collected, separated and purified, further reacted, and/or processed in some other manner.

FIG. 1B illustrates the zone reactor ready for a run in the reverse direction, from right to left. The reactor 10 still contains zones 1-3 and subzones 1A, 1B, 3B, and 3A, but now the material in zone 3A is capable of releasing HX when heated in air or oxygen (having been hydrohalogenated when the reactor was run in the forward direction). Similarly, the catalyst in zone 3B is now coated and/or impregnated with coke, whereas the catalyst in zone 1B has little or (ideally) no coke. The material in zone 1A is ready to react with, and thereby capture and store, HX. Air or oxygen is introduced through the third inlet 6 in zone 3A and causes the material contained therein to release HX, which flows, along with air or oxygen, into zone 3B. The air or oxygen oxidizes the coke that has been deposited on the carbon-carbon coupling catalyst. HX and air or oxygen are carried downstream into zone 2, where they react with the hydrocarbon feedstock to form alkyl halides and steam, which pass into zone 1B. The alkyl halides react in zone 1B in the presence of the carbon-carbon coupling catalyst, and form hydrocarbon products, HX, and coke (which is deposited on and/or in the catalyst). HX, $CO_2$, air or its components, steam, and possibly other gases then pass into zone 1A, and the HX reacts with and is captured by the material contained therein. Products and residual gases exit through the first opening 4. The reactor is again ready to be run in the forward direction. By cycling between the forward and reverse directions, the reactor can be operated continually.

In an alternate embodiment, the flow of gaseous reactants always maintains the same direction, and the reaction zones are stationary. However, the solids are continuously regenerated. As the halide contained within zone 1A is depleted, solid is withdrawn at a constant rate from that zone and transported into zone 3A. Similarly, fully regenerated solid is constantly withdrawn from zone 3A and transported back to zone 1A. The solid transport between zones 1A and 3A is facilitated by gravity, pneumatic transport, other mechanical means (e.g., conveyors), or a combination of methods. In a similar manner, non-regenerated carbon-carbon coupling catalyst in zone 1B is continuously withdrawn and transported to zone 3B, and coked carbon-carbon coupling catalyst is transported from Zone 3B to Zone 1B for regeneration. Transport of the coupling catalyst is facilitated by gravity, pneumatic transport, other mechanical means, or a combination of methods.

As used here and in the claims, the use of the singular or the plural in reference to a compound, catalyst, or other substance is not intended to limit the substance to a particular number of molecules or quantity, nor to a particular number of different types of the substance, unless otherwise indicated. For example, "higher hydrocarbons" can include a quantity of predominately one, or exactly one, compound (e.g., a quantity of isooctane) or two or more different compounds (e.g., butane, benzene, propylene, etc.). Similarly, "olefins" refers to a quantity of a single olefin, or two or more different olefins; "zeolites" refers to a quantity of one or more different zeolites; etc.

It is contemplated that any of a number of hydrocarbon feedstocks will be used in the practice of the present invention. Nonlimiting examples include one or more light alkanes and/or olefins, e.g., methane, ethane, propane, butane, ethylene, propylene, butenes; natural gas; and other mixtures of hydrocarbons. In most embodiments, the feedstock will be primarily aliphatic in nature. Certain oil refinery processes yield light hydrocarbon streams (so-called "light-ends," typically a mixture of C1-C3 hydrocarbons), which can be used with or without added methane. In general, the feedstock is introduced into the reactor as a gas.

The products of the zone reactor—one or more "higher hydrocarbons"—will depend on the feedstock, the carbon-carbon coupling catalyst, and the reactor conditions, e.g., gas flow rates (which affects reactor residence time), temperature, and pressure. As used herein, the term "higher hydrocarbon" refers to a hydrocarbon having a higher carbon number (greater number of carbon atoms per molecule) and/or a higher bond order than one or more components of the hydrocarbon feedstock. For example, if the feedstock is pure methane (carbon number 1, bond order 1), the resulting higher hydrocarbons produced could be ethane, propane, ethylene, propylene, larger alkanes and olefins, possibly alkynes, and/or aromatic compounds. If the feedstock is pure ethane (carbon number 1; bond order 1), the resulting higher hydrocarbons could be propane (carbon number 3; bond order 1), ethylene (carbon number 2, bond order 2), etc. If the feedstock is natural gas—typically a mixture of light hydrocarbons, predominately methane, with lesser amounts of ethane, propane, and butane, and even smaller amounts of longer hydrocarbons such as pentane, hexane, etc.—the resulting higher hydrocarbons could include one or more C2 or higher alkanes (e.g., ethane, propane, butane, C5+ hydrocarbons and other light naphthas); olefins (e.g., ethylene, propylene, butylene, etc.); and/or aromatic hydrocarbons.

Certain classes of higher hydrocarbons are particularly desirable, including "gasoline range" hydrocarbons, e.g., C4-C12 alkanes, more preferably C5-C10 alkanes, with or without olefinic and/or aromatic components. C5+ alkanes with high aromatic content, but low benzene content are particularly desirable as gasolines or gasoline blending agents. Other desirable products include aromatic compounds—benzene, toluene, xylene (especially p-xylene), mesitylene, etc.—and especially aromatic products with low benzene content. In one embodiment, the product consists predominantly of benzene, or benzene-rich aromatics. In another embodiment, the product consists predominantly of toluene, or toluene-rich aromatics. In one embodiment, the aromatic content of the product is enriched by recycling non-aromatic components to the solid reactor. In the case of saturated aliphatic compounds, this entails re-bromination followed by carbon-carbon coupling in the presence of a coupling catalyst, whereas olefinic compounds may be coupled directly (in the presence of a coupling catalyst as described herein.

Representative hydrogen halides (HX) include hydrogen bromide (HBr) and hydrogen chloride (HCl). It is also contemplated that hydrogen fluoride (HF) and hydrogen iodide (HI) can be used, though not necessarily with equivalent results. Some of the problems associated with fluorine can likely be addressed by using dilute streams of HF (e.g., HF gas carried by helium, nitrogen, or other diluent). It is expected, however, that more vigorous reaction conditions will be required for alkyl fluorides to couple and form higher hydrocarbons, due to the strength of the fluorine-carbon bond. Similarly, problems associated with HI (such as the endothermic nature of certain iodine reactions) can likely be addressed by carrying out the halogenation and/or coupling reactions at higher temperatures and/or pressures. The use of HBr or HCl is preferred, with HBr being most preferred.

A number of materials are capable of reversibly capturing and releasing HX and, in particular, HCl and HBr. As a first example, such materials comprise medium- to long-chain olefins, i.e., olefins having 10-100, preferably 15-80, more preferably 20-50 carbon atoms per molecule. In general, such olefins will have more than one carbon-carbon double bond per molecule. Nonlimiting specific examples include 1-dodecene, 1,12-dodecadiene, and i-eicosane. Unsaturated olefins undergo addition reactions with HX to form partially halogenated olefins or alkanes, and thereby "reactively capture" HX. When the materials are heated, they release HX and revert to olefins.

As a second example, unsaturated organic polymers can capture HX to form partially halogenated organic polymers, which, in turn, can release HX. Nonlimiting examples include polyacetylene, polyethylene that has been partially dehydrogenated, polypropylene that has been partially dehydrogenated, and mixtures thereof. Polyethylene and polypropylene can be dehydrogenated according to methods well known to those skilled in the art, e.g., via halogenation followed by dehydrohalogenation. Polybutadiene is another example of an unsaturated organic polymer that may be used to capture, and then release, HX.

Olefins and unsaturated organic polymers capture HX by reacting with it to form partially halogenated compounds. The reaction can be reversed by heating the materials in the presence of air or oxygen. The following equations are nonlimiting examples of the basic scheme:

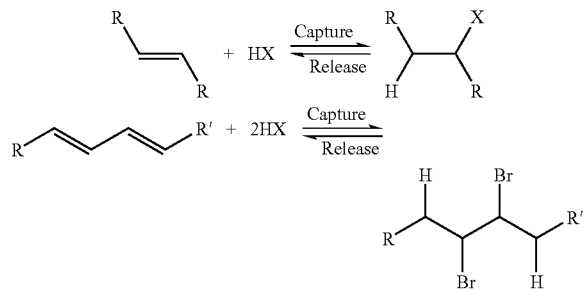

In one embodiment, the unsaturated material is carried on a support, such as silica, titania, or a similar heat-resistant, inorganic, generally inert material. As one example, silica pellets are coated with polyethylene by combining the pellets and polyethylene, heating the mixture to a temperature above the glass transition temperature of the polyethylene, and then adding halogen to the pellets and exposing the combination to ultraviolet light, thereby halogenating the polymer.

In zone 2, alkyl halides are formed by reacting a hydrocarbon feedstock with HX and $O_2$ (oxyhalogenation) and/or by reacting alkyl halides with $X_2$ (halogenation). UV light and/or heat can drive the reaction. In a preferred embodiment, the reaction takes place in the presence of a halogenation and/or oxyhalogenation catalyst or cataloreactant. Nonlimiting examples include metal oxides, such as copper oxide (CuO), and metal halides, such as $CuCl_2$, $CuBr_2$, etc. Mixtures of catalysts can be used. The catalytic materials can be supported or unsupported.

In FIG. 1, the catalyst is located throughout zone 2. In an alternate embodiment shown in FIG. 2, the halogenation and/or oxyhalogenation catalyst is confined to downstream and upstream regions 8 of zone 2, leaving an empty central area 9.

In Zones 1B and 3B, a carbon-carbon coupling catalyst is utilized to facilitate the conversion of alkyl halides to higher hydrocarbons. As used herein, the term "carbon-carbon coupling catalyst" refers to a material capable of catalyzing carbon-carbon bond formation, and includes both "true" catalysts, which presumably participate in the reaction on a mechanistic level, but are not consumed in the process, as well as "cataloreactants," which are chemically transformed in the course of the reaction, but can be returned to their original form via a regeneration reaction. For example, oxygen atoms in the cataloreactant could be replaced by halogen atoms during the carbon-carbon coupling reaction, and then regenerated (with halogen being replaced by oxygen) in a subsequent regeneration step, such as by the passage of air or oxygen over the initially transformed cataloreactant material. Carbon-carbon coupling catalysts are also referred to as "oligomerization catalysts," or simply, "coupling catalysts."

Nonlimiting examples of coupling catalysts include non-crystalline alumino silicates (amorphous solid acids), tungsten/zirconia super acids, sulfated zirconia, alumino phosphates such as SAPO-34 and its framework-substituted analogues (substituted with, e.g., Ni or Mn), Zeolites, such as ZSM-5 and its ion-exchanged analogs, and framework substituted ZSM-5 (substituted with Ti, Fe, Ti+Fe, B, or Ga). and other microporous minerals. The catalysts can be natural or synthetic, doped or undoped, supported or unsupported.

Preferred catalysts for producing liquid-at-room-temperature hydrocarbons include ion-exchanged ZSM-5 having a $SiO_2/Al_2O_3$ ratio of less than 300:1, preferably less than 100:1, and most preferably 30:1 or less. Nonlimiting examples of preferred exchanged ions include ions of Ag, Ba, Bi, Ca, Fe, Li, Mg, Sr, K, Na, Rb, Mn, Co, Ni, Cu, Ru, Pb, Pd, Pt, and Ce. These ions can be exchanged as pure salts or as mixtures of salts. The preparation of doped zeolites and their use as carbon-carbon coupling catalysts is described in Patent Publication No. US 2005/0171393 A1, at pages 4-5, which is incorporated by reference herein in its entirety.

Zeolites are available from a variety of sources, including Zeolyst International (Valley Forge, Pa.). Specific examples include doped-ZSM-5 and doped mordenite (where, e.g., calcium and/or magnesium are the dopants). In one embodiment of the invention a Mn-exchanged ZSM-5 zeolite having a $SiO_2/Al_2O_3$ ratio of 30 is used as the coupling catalyst. Under certain process conditions, it can produce a tailored selectivity of liquid hydrocarbon products.

Product distribution can be shifted in favor of more aromatic content, less aromatic content, gasoline grade materials by altering the properties of the zeolite or other catalyst. Pore size and acidity are expected to be important. Acidity may be used to control product chain length and functionality, and pore size may control chain length and functionality. Zeolites having a particular pore size may selectively produce benzene, toluene, para-xylene, ortho-xylene, meta-xylene, mixed xylenes, ethylbenzene, styrene, linear alkylbenzene, and/or other aromatic products. Pore size can also be expected to affect formation of non-aromatic products.

In various aspects of the invention, air or oxygen is used to accomplish a desired result, for example, decoking, oxyhalogenation, HX release, cataloreactant regeneration, etc. It is to be understood that the term "air or oxygen" in this context includes any of a number of oxygen-based or oxygen-containing gas streams. Nonlimiting examples include ordinary air, pure oxygen gas ($O_2$), oxygen gas containing minor amounts of other gaseous components, dilute streams of oxygen gas in a carrier gas (e.g., helium), oxygen-enriched air, etc.

To facilitate the various steps of HX capture and release, catalyst decoking, halogenation and/or oxyhalogenation, and product formation, different zones of the reactor are operated at appropriate pressures and temperatures, taking into account the feedstock, catalysts, gas flow rates, and desired product(s). In one embodiment, the reactor is operated at, or slightly above, atmospheric pressure. Zone 1A or 3A is heated to a temperature of from 0 to 500° C., preferably 100 to 400° C., more preferably 200 to 300° C., to facilitate HX release. Zone 3A or 1A is heated to a slightly lower temperature, e.g., 0 to 400° C., preferably 100 to 300° C., more preferably 150 to 250° C., to facilitate HX capture. Decoking of the coupling catalyst is facilitated by heating zone 1B or 3B to a higher temperature, e.g., about 500° C. Halogenation and/or oxyhalogenation of the hydrocarbon feedstock occurs in zone 2, which is heated to a temperature of 150 to 600° C., preferably 400 to 600° C., more preferably 450 to 515° C. Product formation (carbon-carbon coupling) is facilitated by heating zone 3B or 1B to a temperature of 150 to 600° C., preferably 275 to 425° C.

There are a number of alternate embodiments for practicing the invention. For example, instead of a single vessel defining three zones, the zone reactor can comprise three separate vessels, each defining a separate zone, 1, 2, or 3. As another example, certain reactor designs offer the possibility of improved heat transfer. Thus, the reactor can be configured as a series of small tubes (inner diameter less than 6 inches, more preferably from 2 to 4 inches). As a third example, instead of an in-line configuration, the tubes can be arranged in parallel and enclosed in a larger vessel, in which a suitable heat transfer fluid is circulated. Alternatively, the bundle of tubes can have air or another inert gas directed across their surface to facilitate cooling and/or heating.

In some applications, where the outlet from zone 2 must be cooled before entering the product formation (metathesis) zone (zone 1B or 3B), a precooler can be used. In one embodiment, the precooler comprises an air-cooled bundle of tubes, or tubes enclosed in a shell in which a suitable heat transfer fluid is circulated around the tubes. The use of a precooler can decrease the required reactor volume in the metathesis zone. The requirement of heat removal during metathesis can strongly influence reactor design.

Another alternative is to use an inert heat carrier within the interior of the reactor itself. For example, an excess of alkane feedstock can be introduced to dissipate the heat, thereby allowing the reactor to be in a packed bed configuration instead of a tube-shell arrangement. The use of an internal heat carrier should allow the reactor to be operated adiabatically. An inert stream that can be separated easily from the reaction product stream can also be used as a heat carrier in this configuration. It is expected that an adiabatic packed bed scheme can significantly reduce reactor cost.

In still another embodiment of the invention, a zone reactor is used in combination with a post-reactor bed packed with ZSM-5 zeolites or other materials that facilitate production of gasoline-range hydrocarbons. For example, a zone reactor can be used to form light olefins, which are then fed into a zeolite bed to facilitate coupling of the light olefins into gasoline-range hydrocarbons.

A number of materials of construction may be employed to enhance the lifetime of the zone reactor. Nonlimiting examples include Hastelloy alloys, aluminum- and chromium-enriched metal alloys, titanium, zirconium, tantalum and nickel metal and their alloys, silica-, alumina-, and zirconia-coated metals, and heat conducting ceramic materials such as silicon carbide. Reactor vessels also can be constructed of insulating, corrosion-resistant materials, for example, alumina, silica, and zirconia, each lined with a corrosion-resistant, but not necessarily temperature-resistant, material, such as polytetrafluoroethylene. Under some conditions, the vessel can be operated isothermally, with heating and/or cooling provided by a heat transfer fluid passed through pipes constructed of the types of heat-conducting materials listed above. Alternatively, the reactor can be operated adiabatically.

EXAMPLES

The following are nonlimiting examples of the invention.
Preparation of Materials Capable of Releasing and Capturing HBr
Reagents A and B High surface area (>300 m2/g) silica pellets are coated with polyethylene by combining the pellets and polyethylene and heating to a temperature above the glass transition temperature of the polyethylene. Bromine is added to the pellets and the combination is exposed to UV light, resulting in bromination of the polymer. Half of the material is separated and heated to 225° C., resulting in the release of HBr and formation of a material, Reagent A, capable of capturing HBr. The other half of the material, Reagent B, is kept for use as a material capable of releasing HBr.
Reagents C and D
Formation of an adsorbent. High surface area (>300 m2/g) silica pellets are coated with polyethylene by combining the pellets and polyethylene and heating to a temperature above the glass transition temperature of the polyethylene. Chlorine is added to the pellets and the combination is exposed to UV light, resulting in chlorination of the polymer. Half of the material is separated and heated to 225° C., resulting in the release of HCl. The other half of the material is kept for use an HCl-containing adsorbent.

Example 1

A zone reactor as shown in FIG. 1 is loaded with the following materials:
Zone 1A: Reagent B.
Zone 1B: ZSM-5 coupling catalyst.
Zone 2: copper oxide catalyst.
Zone 3B: ZSM-5 coupling catalyst.
Zone 3A: Reagent A.
In step 1, air is passed through zone 1A at a temperature of 225° C., converting Reagent B to Reagent A and releasing HBr. The air and HBr from zone 1A pass first into zone 1B at a temperature of 500° C. (in subsequent runs this will regenerate (decoke) the coupling catalyst), and then into zone 2, where natural gas is oxybrominated at 400° C. The products of zone 2 pass over the coupling catalyst in zone 3B at 400° C., producing higher hydrocarbon and HBr. In zone 3A, HBr is captured by Reagent A (which is converted to Reagent B) at a temperature of 150° C.

In step 2, air is passed through zone 3A at a temperature of 225° C., converting Reagent B to Reagent A and releasing HBr. The air and HBr from zone 3A pass into zone 3B at a temperature of 500° C., regenerating (decoking) the coupling catalyst. In zone 2, natural gas is oxybrominated at 400 C. The products of zone 2 pass over the coupling catalyst in zone 1B at 400° C. producing higher hydrocarbons and HBr. In zone 1A, HBr is captured by Reagent A (which is converted to Reagent B) at a temperature of 150° C.

Example 2

The hydrocarbon products of Example 1 are passed over a ZSM-5 catalyst at a temperature of 350 to 450° C., so as to change the average molecular weight of the products.

Example 3

The procedure of example 1 is followed, but instead of ZSM-5, a mixture of tungsten oxide and zirconia (WZA) is used as the carbon-carbon coupling catalyst.

Example 4

The hydrocarbon products of Example 3 are passed over a ZSM-5 catalyst at a temperature of 350 to 450° C., so as to change the average molecular weight of the products.

Example 5

A zone reactor as shown in FIG. 1 is loaded with the following materials:

Zone 1A: Reagent D.
Zone 1B: ZSM-5 coupling catalyst.
Zone 2: copper oxide catalyst.
Zone 3B: ZSM-5 coupling catalyst.
Zone 3A: Reagent C.

In step 1, air is passed through zone 1A at a temperature of 225° C., converting Reagent D to Reagent C and releasing HCl. The air and HCl from zone 1A pass into zone 1B at a temperature of 500° C. (in subsequent runs, this will regenerate (decoke) the coupling catalyst), and then into zone 2, where natural gas is oxychlorinated at 400° C. The products of zone 2 pass over the coupling catalyst in zone 3B at 400° C., producing higher hydrocarbon and HCl. In zone 3A, HCl is captured by Reagent C (which is converted to Reagent D) at a temperature of 150° C.

In step 2, air is passed through zone 3A at a temperature of 225° C., converting Reagent D to Reagent C and releasing HCl. The air and HCl from zone 3A pass into zone 3B at a temperature of 500° C., regenerating (decoking) the coupling catalyst. In zone 2, natural gas is oxychlorinated at 400° C. The products of zone 2 pass over the coupling catalyst in zone 1B at 400° C., producing higher hydrocarbons and HCl. In zone 1A, HCl is captured by Reagent C (which is converted to Reagent D) at a temperature of 150° C.

Example 6

The hydrocarbon products of Example 5 are passed over a ZSM-5 catalyst at a temperature of 350 to 450° C., so as to change the average molecular weight of the product.

Example 7

The procedure of example 5 is followed, but instead of ZSM-5, a mixture of tungsten oxide and zirconia (WZA) is used as the carbon-carbon coupling catalyst.

Example 8

The hydrocarbon products of Example 7 are passed over a ZSM-5 catalyst at a temperature of 350 and 450° C., so as to change the average molecular weight of the products.

The invention has been described with reference to various embodiments, figures, and examples, but is not limited thereto. Persons having ordinary skill in the art will appreciate that the invention can be modified in a number of ways without departing from the invention, which is limited only by the appended claims and equivalents thereof.

What is claimed is:

1. A reactor for converting a hydrocarbon feedstock into one or more products, comprising:
   one or more hollow vessels that define multiple zones in the reactor, wherein a first zone contains a material capable of releasing hydrogen halide and a carbon-carbon coupling catalyst, a second zone is coupled to the first zone, and a third zone is coupled to the second zone and contains a carbon-carbon coupling catalyst and a material capable of capturing hydrogen halide.

2. A reactor as recited in claim 1, wherein the reactor comprises a single vessel and the first zone is located at a first end of the vessel, the second zone is located in the middle of the vessel, and the third zone is located at a second end of the vessel, and wherein gas can flow from the first zone to the second zone and from the second zone to the third zone.

3. A reactor as recited in claim 1, wherein the first zone is located in a first vessel, the second zone is located in a second vessel, and the third zone is located in a third vessel, and wherein gas can flow from the first zone to the second zone and from the second zone to the third zone.

4. A reactor as recited in claim 1, wherein the material capable of releasing hydrogen halide in the first zone is located in a first subzone in the first zone, the carbon-carbon coupling catalyst in the first zone is located in a second subzone in the first zone, the carbon-carbon coupling catalyst in the third zone is located in a first subzone in the third zone, and the material capable of capturing hydrogen halide in the third zone is located in a second subzone in the third zone.

5. A reactor as recited in claim 1, wherein the material capable of releasing hydrogen halide in the first zone comprises partially halogenated olefins.

6. A reactor as recited in claim 5, wherein the partially halogenated olefins have 10-100 carbon atoms per molecule.

7. A reactor as recited in claim 5, wherein the partially halogenated olefins have 15-80 carbon atoms per molecule.

8. A reactor as recited in claim 5, wherein the partially halogenated olefins have 20-50 carbon atoms per molecule.

9. A reactor as recited in claim 5, wherein the partially halogenated olefins comprise at least one material selected from the group consisting of partially halogenated 1-dodecene, partially halogenated 1,12-dodecadiene, partially halogenated 1-eicosane, and mixtures thereof.

10. A reactor as recited in claim 1, wherein the material capable of releasing hydrogen halide in the first zone comprises partially halogenated organic polymers.

11. A reactor as recited in claim 10, wherein the partially halogenated organic polymers comprise at least one material selected from the group consisting of partially halogenated polyacetylene, polyethylene that has been partially dehydrogenated and partially halogenated, polypropylene that has been partially dehydrogenated and partially halogenated, and mixtures thereof.

12. A reactor as recited in claim 10, wherein the partially halogenated organic polymers comprise partially halogenated polybutadiene.

13. A reactor as recited in claim 1, wherein the material capable of capturing hydrogen halide in the third zone comprises olefins that have 10-100 carbon atoms per molecule.

14. A reactor as recited in claim 13, wherein the olefins have 15-80 carbon atoms per molecule.

15. A reactor as recited in claim 13, wherein the olefins have 20-50 carbon atoms per molecule.

16. A reactor as recited in claim 1, wherein the material capable of capturing hydrogen halide in the third zone comprises unsaturated organic polymers.

17. A reactor as recited in claim 16, wherein the unsaturated organic polymers comprise at least one material selected from the group consisting of polyacetylene, polyethylene that has been partially dehydrogenated, polypropylene that has been partially dehydrogenated, and mixtures thereof.

18. A reactor as recited in claim 16, wherein the unsaturated organic polymers comprise polybutadiene.

19. A reactor as recited in claim 1, wherein the second zone contains a halogenation catalyst, an oxyhalogenation catalyst, or a mixture thereof.

20. A reactor as recited in claim 19, wherein the halogenation and/or oxyhalogenation catalyst comprises copper oxide.

21. A reactor as recited in claim 19, wherein the halogenation and/or oxyhalogenation catalyst comprises a copper halide.

22. A reactor as recited in claim 21, wherein the copper halide comprises copper bromide or copper chloride.

23. A reactor as recited in claim 1, wherein the carbon-carbon coupling catalyst in the first zone or the carbon-carbon coupling catalyst in the third zone comprises a microporous material.

24. A reactor as recited in claim 23, wherein the microporous material comprises supported or unsupported zeolites.

25. A reactor as recited in claim 24, wherein the zeolites comprise doped zeolites.

26. A reactor as recited in claim 24, wherein the zeolites comprise ZSM-5-type zeolites.

27. A reactor as recited in claim 1, wherein the first, second, and third zones are located inside a single hollow vessel; the first and second zones are separated by a first divider having at least one opening therein; and the second and third zones are separated by a second divider having at least one opening therein.

28. A reactor as recited in claim 27, wherein the first and second dividers comprise a screen.

29. A reactor for converting a hydrocarbon feedstock into higher hydrocarbons, comprising:
a hollow vessel having first, second, and third zones, wherein the first zone contains ZSM-5 zeolites and a material capable of releasing hydrogen halide selected from the group consisting of partially halogenated olefins, partially halogenated organic polymers, and a mixture thereof; the second zone is coupled to the first zone and contains a metal oxide; and the third zone is coupled to the second zone and contains a microporous carbon-carbon coupling catalyst and a material capable of capturing hydrogen halide selected from the group consisting of olefins, unsaturated organic polymers, and a mixture thereof.

30. A reactor as recited in claim 29, wherein the metal oxide comprises copper oxide.

31. A reactor as recited in claim 29, wherein the microporous carbon-carbon coupling catalyst comprises ZSM-5 zeolites.

32. A reactor as recited in claim 29, wherein the material capable of releasing hydrogen halide in the first zone is located in a first subzone in the first zone; the ZSM-5 zeolites are located in a second subzone in the first zone; the microporous carbon-carbon coupling catalyst is located in a first subzone in the third zone; and the material capable of capturing hydrogen halide in the third zone is located in a second subzone in the third zone.

* * * * *